(12) United States Patent
Chang

(10) Patent No.: US 11,305,078 B2
(45) Date of Patent: Apr. 19, 2022

(54) VENTILATOR

(71) Applicant: Invent Medical Corporation, Carlsbad, CA (US)

(72) Inventor: Samuel M. Chang, Poway, CA (US)

(73) Assignee: INVENT MEDICAL CORPORATION, Carlsbad, CA (US)

( * ) Notice: Subject to any disclaimer, the term of this patent is extended or adjusted under 35 U.S.C. 154(b) by 0 days.

(21) Appl. No.: 16/426,275

(22) Filed: May 30, 2019

(65) Prior Publication Data

US 2019/0275273 A1    Sep. 12, 2019

Related U.S. Application Data

(63) Continuation of application No. 15/087,522, filed on Mar. 31, 2016, now abandoned.
(Continued)

(51) Int. Cl.
*A61M 16/00*     (2006.01)
*A61M 16/10*     (2006.01)
(Continued)

(52) U.S. Cl.
CPC .... *A61M 16/0066* (2013.01); *A61M 16/0051* (2013.01); *A61M 16/0057* (2013.01);
(Continued)

(58) Field of Classification Search
CPC ............ A61M 16/0066; A61M 16/026; A61M 16/202; A61M 16/0057; A61M 16/0051; A61M 16/205; A61M 16/204; A61M 16/12; A61M 16/1005; A61M 16/1055; A61M 16/208; A61M 16/0003; A61M 16/0015; A61M 16/0027; A61M 16/003; A61M 16/00; A61M 16/04; A61M 16/0486; A61M 16/0488; A61M 16/06; A61M 16/10; A61M 16/1015; A61M 16/105; A61M 16/20;
(Continued)

(56) References Cited

U.S. PATENT DOCUMENTS 3,831,595 A * 8/1974 Valenta ............. A61M 16/0051
                                                                    128/202.22
4,022,234 A * 5/1977 Dobritz ................ G05D 11/133
                                                                    137/7
(Continued)

*Primary Examiner* — Justine R Yu
*Assistant Examiner* — Matthew D Ziegler
(74) *Attorney, Agent, or Firm* — Procopio, Cory, Hargreaves & Savitch LLP

(57) ABSTRACT

This invention provides ventilators that provide superior air-oxygen mixing and gas delivery. The ventilators that supply a gas mixture to the lungs of a subject. The gas mixture comprises a first gas (e.g. oxygen) and a second gas (e.g. ambient air). The ventilators comprise a first gas inlet, a second gas inlet, flow modulator of the first gas, a flow modulator of the second gas, a junction configured to mix the first gas and the second gas, a patient interface configured to deliver the gas mixture to a subject, a pressure sensor, a plurality of flow sensors comprising at least a first flow sensor and a second flow sensor, and at least one controller configured for obtaining data from the pressure sensor and flow sensors and controlling the flow modulators to provide a gas mixture having a target pressure and a target oxygen content.

22 Claims, 11 Drawing Sheets

Related U.S. Application Data

(60) Provisional application No. 62/143,026, filed on Apr. 3, 2015.

(51) Int. Cl.
*A61M 16/12* (2006.01)
*A61M 16/20* (2006.01)

(52) U.S. Cl.
CPC ...... *A61M 16/026* (2017.08); *A61M 16/1005* (2014.02); *A61M 16/12* (2013.01); *A61M 16/202* (2014.02); *A61M 16/204* (2014.02); *A61M 16/205* (2014.02); *A61M 16/1055* (2013.01); *A61M 16/208* (2013.01); *A61M 2016/0027* (2013.01); *A61M 2016/0036* (2013.01); *A61M 2016/0039* (2013.01); *A61M 2016/1025* (2013.01); *A61M 2202/0208* (2013.01); *A61M 2202/0241* (2013.01); *A61M 2202/0266* (2013.01); *A61M 2202/0291* (2013.01); *A61M 2205/3331* (2013.01); *A61M 2205/3355* (2013.01); *A61M 2205/50* (2013.01); *A61M 2205/7518* (2013.01); *A61M 2230/04* (2013.01); *A61M 2230/06* (2013.01); *A61M 2230/10* (2013.01); *A61M 2230/205* (2013.01); *A61M 2230/30* (2013.01); *A61M 2230/432* (2013.01); *A61M 2230/50* (2013.01)

(58) Field of Classification Search
CPC ........ A61M 16/201; A61M 2016/0036; A61M 2016/1025; A61M 2016/0039; A61M 2016/0027; A61M 2016/102; A61M 2230/432; A61M 2230/50; A61M 2230/10; A61M 2230/30; A61M 2230/205; A61M 2230/04; A61M 2230/06; A61M 2230/40; A61M 2230/42; A61M 2230/43; A61M 2230/435; A61M 2202/0208; A61M 2202/0241; A61M 2202/0266; A61M 2202/0291; A61M 2205/3331; A61M 2205/3355; A61M 2205/50; A61M 2205/7518; A61M 2205/07; A61M 2205/33; A61M 2205/75; A61M 2210/06; A61M 2210/0625; A61M 39/00; A61M 39/10; A61M 39/22; A61M 39/24; A61M 16/0063; A61M 16/0069; A61M 16/021; A61M 16/022; A61M 16/024; A61M 16/125; A61M 16/122

See application file for complete search history.

(56) References Cited

U.S. PATENT DOCUMENTS

| | | | | |
|---|---|---|---|---|
| 4,072,148 A | * | 2/1978 | Munson | A61M 16/12 128/205.11 |
| 4,127,121 A | * | 11/1978 | Westenskow | A61M 16/104 128/203.14 |
| 4,392,514 A | * | 7/1983 | Farley | G05D 11/132 137/607 |
| 4,448,192 A | * | 5/1984 | Stawitcke | A61M 16/0051 128/204.23 |
| 5,299,568 A | * | 4/1994 | Forare | A61M 16/12 128/205.11 |
| 5,303,698 A | * | 4/1994 | Tobia | A61M 16/024 128/204.21 |
| 5,664,560 A | * | 9/1997 | Merrick | A61M 16/202 128/203.25 |
| 5,823,186 A | * | 10/1998 | Rossen | A61M 16/0063 128/204.21 |
| 5,848,591 A | * | 12/1998 | Weismann | A61M 16/12 128/204.22 |
| 6,148,816 A | * | 11/2000 | Heinonen | A61M 16/024 128/205.24 |
| 8,047,205 B2 | * | 11/2011 | von Blumenthal | A61M 16/12 128/205.11 |
| 10,617,836 B2 | * | 4/2020 | Kagan | A61M 16/0066 |
| 2007/0125374 A1 | * | 6/2007 | Smith | A61M 16/204 128/203.12 |
| 2010/0224192 A1 | * | 9/2010 | Dixon | A61B 5/02416 128/204.23 |
| 2012/0006326 A1 | * | 1/2012 | Ahmad | A61M 16/024 128/204.22 |
| 2014/0005566 A1 | * | 1/2014 | Homuth | A61B 5/087 600/538 |
| 2015/0273176 A1 | * | 10/2015 | Acker | A61M 16/024 128/202.22 |

* cited by examiner

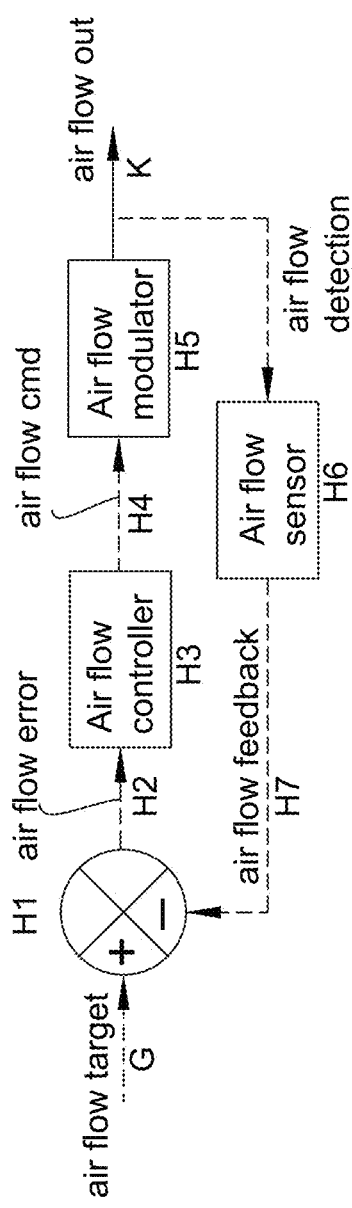
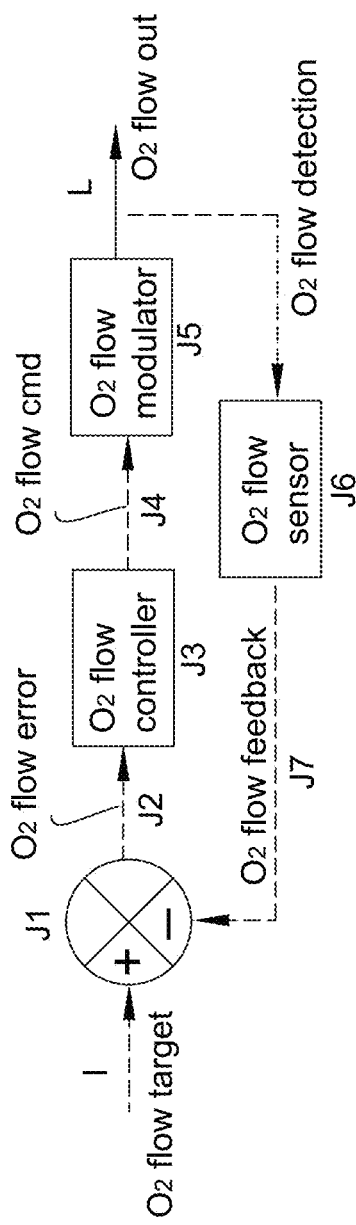
Fig. 6A
Fig. 6B

VENTILATOR

CROSS-REFERENCE TO RELATED APPLICATIONS

This application is a continuation of U.S. non-provisional application Ser. No. 15/087,522 filed on Mar. 31, 2016, which claims priority to U.S. provisional application No. 62/143,026 filed on Apr. 3, 2015, both of which are incorporated herein by reference in their entireties.

TECHNICAL FIELD

The present invention relates to ventilators.

BACKGROUND

A ventilator delivers a flow of gas such as air, which is usually pressurized, to the airway of a patient to assist in or substitute a patient's breathing. Ventilators can be configured to operate cyclically, for example, by providing gas to the patient during an inhalation phase and returned from the patient during a subsequent exhalation phase. Some ventilators mix oxygen and air for inspiration such that the patient receives a mixed gas with a target oxygen content greater than ambient air.

Ventilators can be designed to be leak-free or to have intentional leaks. In any design, accurate metering of gas and air/oxygen mixing can be dramatically affected by an unintentional leak. Most often, the exhalation valve on a leak-free ventilator is provided on an exhalation limb of the ventilator at the patient interface such that expiration gas exits through the exhalation valve. This second limb adds to the bulk, weight, and production cost of ventilators. Some single-limb ventilators vent the expiration gas to atmosphere after it has traveled upstream in the inspiration line as well as through the exhalation port proximal to the patient. One of the shortcomings of these single-limb ventilators is cross contamination of the ventilator as well as high exhalation resistance.

In addition to being designed as leak-free, ventilators with the most accurate mixing of air and oxygen and delivery of pressurized gas to the patient have used a source of high pressure oxygen source and a source of high pressure air. The high pressure sources are either pressurized tanks or the high pressure lines of a hospital via a compressor. These types of ventilators are typically not mobilized for extended durations given the size of the air tank that would be required for sustained ventilation.

Some ventilators circumvent the need for hospital line or air tank air by providing a compressor or other air pump as the source of pressurized air. Air pump ventilators that have been able to produce satisfactory air/oxygen mixing and delivery requirements use positive displacement pumps such as roots blowers, screw compressors, piston compressors and scroll compressors, which are typically configured to produce high pressure air. However, these positive displacement pumps are typically noisy, causing discomfort and disturbance to patients and support personnel.

One alternative approach has been to use low pressure dynamic pumps. These pumps can operate with lower noise output but have generally failed to provide high pressure and air-oxygen mixing requirements. Some of these ventilators combine low flow oxygen with low pressure air while others combine high pressure oxygen with low pressure air. The ventilators that provide low flow oxygen fail to meet the oxygen content for certain patients that require high oxygen mixing. The ventilators that provide high pressure oxygen and low pressure air often have failed to provide a combination of pneumatic hardware and control algorithm that yield satisfactory accuracy for real-time mixing.

Philips Respironics has produced one ventilator in its BiPAP Vision line that has combined a high pressure oxygen source with a low pressure centrifugal dynamic pump. While this ventilator can produce a mixture having a satisfactory pressure, it has failed to produce superior accuracy of air/oxygen mixing. Further, to achieve pressure targets, this ventilator uses what Philips calls an in-line flow restrictor and a pressure regulation valve, neither of which is closed completely during inspiration or exhalation. Philips does not teach an exhalation valve that is closed during the inhalation phase. Additionally, Philips does not teach a ventilator comprising a mixing chamber or a ventilator comprising a pump downstream of an air/oxygen junction.

Rossen et al. (U.S. Pat. No. 5,823,186) describe a respirator having an inspiration line fed by an air line having a compressor and an oxygen line, wherein the oxygen line comprises a metering unit and the air line comprises a flow sensor. Rossen et al. do not teach a ventilator having any of the following features: a dynamic pump, a proportional valve in the oxygen line, or a single limb configuration with an exhalation valve and a check valve upstream of the exhalation valve.

Hete et al. (US 20070044799) describe a gas delivery system that generates a pressurized flow of breathable gas and includes a primary gas delivery system and a supplemental gas delivery system. The primary gas can be air. The supplemental gas can be oxygen. The primary gas can be drawn in in by a pressure generator. Hete et al. do not teach a ventilator having any of the following features: a dynamic pump, a pressure sensor downstream of an oxygen/air junction, a check valve downstream of a pump in an air line, or a check valve upstream of an exhalation valve.

Von Blumenthal et al. (U.S. Pat. No. 8,047,205) describe a gas mixing device for respirators. The gas-mixing device has a storage tank into which compressed air and oxygen can be introduced by dispensing valves and also has a blower which draws in gas from the environment to the storage tank. Von Blumenthal et al. do not teach a ventilator having any of the following features: a dynamic pump, a flow sensor in an oxygen line, a flow sensor in an air line, a pressure sensor downstream of the storage tank, a flow sensor downstream of the storage tank, a proportional valve on an air line or an oxygen line which feed a storage tank.

Richardson et al. (U.S. Pat. No. 6,279,574) describe a ventilator having a reservoir that receives compressed air and oxygen. Richardson et al. do not teach a ventilator having any of the following features: a pump that conveys air to the reservoir, a flow sensor downstream of the reservoir, a controller that calculates flows of air and oxygen to obtain a target oxygen content and pressure.

Ahmad (US 20120006326) describes a ventilator having a first pathway and a second pathway that merge to provide a mixed gas. Ahmad does not teach a ventilator having any of the following features: a dynamic pump, a flow sensor downstream of the pump, a check valve in an air line, or an exhalation valve in a mixed gas line downstream of a pump.

What is need in the art is an economical pump-based ventilator that can be coupled to a high pressure oxygen source and produces oxygen-air mixing and volume- or pressure targeting with superior accuracy.

SUMMARY OF THE INVENTION

This invention provides ventilators that supply a gas mixture to the lungs of a subject. The gas mixture comprises a first gas (e.g. oxygen) and a second gas (e.g. ambient air). The ventilators comprise a first gas inlet, a second gas inlet, flow modulator of the first gas, a flow modulator of the second gas, feed lines that transmit respective gases from the first inlet and the second inlet to a junction, a patient interface configured to deliver the gas mixture to a subject, a pressure sensor, a plurality of flow sensors comprising at least a first flow sensor and a second flow sensor, and at least one controller configured for obtaining data from the pressure sensor and the flow sensors and controlling the flow modulators to provide a gas mixture having a target pressure and a target oxygen content. The flow modulator of the first gas is optionally a valve. The flow modulator of the second gas is optionally a valve or a variable speed pump. In general, gas flows from upstream components (e.g. gas inlets) to downstream components (e.g. patient interface) during patient inhalation. Optionally, the system is configured to allow gas to flow from downstream components (e.g. patient interface) to upstream components (e.g. exhalation valve) during patient exhalation.

A ventilator of the invention optionally comprises:
a. an oxygen inlet;
b. an air inlet;
c. a junction downstream of the oxygen inlet and the air inlet;
d. a patient interface downstream of the junction;
e. a first conduit configured to convey oxygen from the oxygen inlet to the junction ('oxygen line');
f. a second conduit configured to convey air from the air inlet to the junction ('air line');
g. a third conduit configured to convey a gas mixture from the junction to the patient ('mixed gas line'), wherein the gas mixture comprises oxygen from the oxygen line and air from the air line;
h. a pump, wherein the pumped gas at least comprises the air;
i. an air flow modulator, wherein the air flow modulator is configured to modulate at least the flow of air through the air line, optionally wherein the pump is a variable speed pump and the air flow modulator comprises the pump;
j. an oxygen flow modulator, wherein the oxygen flow modulator comprises a first control valve comprised by the oxygen line ('oxygen control valve');
k. a first flow sensor comprised by the oxygen line ('oxygen flow sensor');
l. a second flow sensor, wherein the second flow sensor is comprised by the air line or the mixed gas line; and
m. a controller configured to:
  i. obtain feedback from the first flow sensor and the second flow sensor; and
  ii. control the oxygen control valve and the air flow modulator, e.g. to obtain a target oxygen content.

Optionally, the ventilator comprises a first pressure sensor comprised by the mixed gas line and the controller is configured to obtain feedback from the first pressure sensor and control the air flow modulator and optionally the oxygen control valve, e.g. to obtain a target pressure.

In a first aspect of the invention, the pump is a variable speed pump (e.g. variable speed blower) controlled by the controller and comprised by the air line. Optionally, the second flow sensor is comprised by the air line ('air flow sensor'), e.g. downstream of the pump. Optionally, the ventilator further comprises an exhalation valve, wherein the exhalation valve is downstream of the pump (e.g. upstream of the junction) and is controlled by the controller, and wherein the ventilator further comprises a first check valve downstream of the pump and upstream of the exhalation valve. Optionally, the air flow sensor is downstream of the exhalation valve.

In a second aspect of the invention, the pump is a variable speed pump (e.g. blower) controlled by the controller and comprised by the mixed gas line. Optionally, the ventilator further comprises a check valve comprised by the air line ('air line check valve'). Optionally, the second flow sensor is comprised by the mixed gas line ('mixed gas flow sensor'), e.g. downstream of the variable speed pump. Optionally the oxygen control valve is a proportional valve such as a proportional solenoid valve.

In a third aspect of the invention, the junction comprises a mixing chamber and a second control valve, wherein the second control valve is a proportional valve comprised by the mixed gas line downstream of the mixing chamber ('mixed gas control valve'), wherein the mixed gas control valve is controlled by the controller. Optionally, the second flow sensor is a flow sensor comprised by the air line ('air flow sensor'). Optionally, the mixing chamber is a fixed volume chamber. Optionally, the mixing chamber (e.g. fixed volume chamber) comprises a volume of at least about 300 ml, e.g. about 300 ml to about 5000 ml. Optionally, the mixing chamber comprises a pressure sensor. Optionally, the controller is configured to pressurize the mixing chamber to a pressure of about 10 mbar to about 30 mbar above the target pressure. Optionally, the mixing chamber comprises an oxygen sensor. Optionally, the mixed gas line comprises a flow sensor, a pressure sensor, or both. Optionally, the ventilator comprises an exhalation valve downstream of the mixing chamber and upstream of the patient interface (e.g. wherein the exhalation valve is controlled by the controller) and the ventilator further comprises a check valve is downstream of the mixing chamber and upstream of the exhalation valve. Optionally, the controller is configured to control the flow of at least one of air through the air line and oxygen through the oxygen line. Optionally, the oxygen line comprises a check valve (e.g. downstream of the oxygen control valve) and the air line comprises a check valve (e.g. downstream of the pump). Optionally, the pump is a variable speed pump or the ventilator comprises a third control valve, wherein the third control valve is comprised by the air line and is downstream of the pump (e.g. a constant speed pump).

The present invention contemplates ventilators according to any aspect of the invention. For example, the invention contemplates a ventilator according to the first aspect or, alternatively, according to the second aspect. A ventilator according to the third aspect of the invention can optionally be provided, e.g. in conjunction with, or as an alternative to, the first aspect of the invention or the second aspect of the invention.

In any aspect of the invention, the pump is optionally a blower such as a pump comprising an impeller ('fan blower'). For example, the pump can be a fan blower, wherein the fan blower is a small pump and/or a low pressure pump.

In any aspect of the invention, the ventilator comprises at least one conduit through which gas flows downstream during an inhalation phase and upstream during an exhalation phase ('bidirectional conduit'). Optionally, the bidirectional conduit comprises an exhalation valve wherein the exhalation valve is downstream of the pump, upstream of the patient interface, and controlled by the controller, and optionally, the ventilator further comprises a check valve downstream of the pump and upstream of the exhalation valve. Optionally, the exhalation valve is upstream of the second flow sensor. Optionally, the exhalation valve is a control valve, wherein the controller is configured to open the exhalation valve during an exhalation phase and close the valve during an inhalation phase.

In any aspect of the invention, the mixed gas line optionally comprises a pressure sensor.

In any aspect of the invention, the oxygen line optionally comprises a pressure regulator, wherein the pressure regulator is upstream of the oxygen control valve.

In any aspect of the invention, the oxygen flow sensor is optionally downstream of the oxygen control valve.

In any aspect of the invention, the patient interface optionally comprises a mask, a mouth piece, a nasal prong, or a patient tube such as a tracheal tube (e.g. an endotracheal tube or a tracheostomy tube).

In any aspect of the invention, the controller is optionally configured to use one or more feedback control loops. For example, the controller is optionally configured to use a cascaded feedback control loop comprising an outer feedback loop and one or more inner feedback loops, wherein the command of the outer feedback loop is used to provide a target of the one or more inner feedback loops.

BRIEF DESCRIPTION OF THE DRAWINGS

FIG. 6A depicts an air flow feedback control loop used by an air flow controller useful in the present invention.
FIG. 6B depicts an oxygen flow feedback control loop used by an oxygen flow controller useful in the present invention.

DETAILED DESCRIPTION OF THE INVENTION

As used here, the following definitions and abbreviations apply.

"Exemplary" (or "e.g." or "by example") means a non-limiting example.
Controller A ventilator of the present invention comprises a controller configured for receiving data ('feedback') from sensors and controlling flow modulators to produce a gas mixture exhibiting one or more parameter targets. The parameter targets of the gas mixture at least a target oxygen content (e.g. $FiO_2$). Optionally, the parameter targets of the gas mixture comprise a target pressure, a target volume, a target flow or a combination thereof.

In general, a controller can be configured to control (i.e. send data or analog signals to and/or receive data or analog signals from) output devices and input devices (collectively referred to as 'I/O devices') or another controller of the ventilator. Output devices can include, e.g. flow modulators and a user interface ('UI'). Input device devices can include, e.g. sensors and a UI.

Any controller is useful in the present invention. Optionally, the controller comprises a microcontroller such as a microprocessor or an analog controller. A controller of the present invention can optionally comprise or be connected to one at least one non-volatile memory device having a compilation of executable instructions ('module') configured for causing at least one processor to control I/O devices.

The controller can optionally be a single controller connected to and configured to control the I/O devices or, or alternatively, can comprise a collection of interacting controllers in communication with each other or with a common controller. Optionally, the controller comprises, as interacting controllers, a gas mixture controller, an air flow controller, and an oxygen flow controller. For example, the controller can comprise a plurality of interacting controllers that are independent hardware (e.g. microprocessors) in communication with each other, independent modules that which reference each other, or subroutines of a single module.

Figure 5:
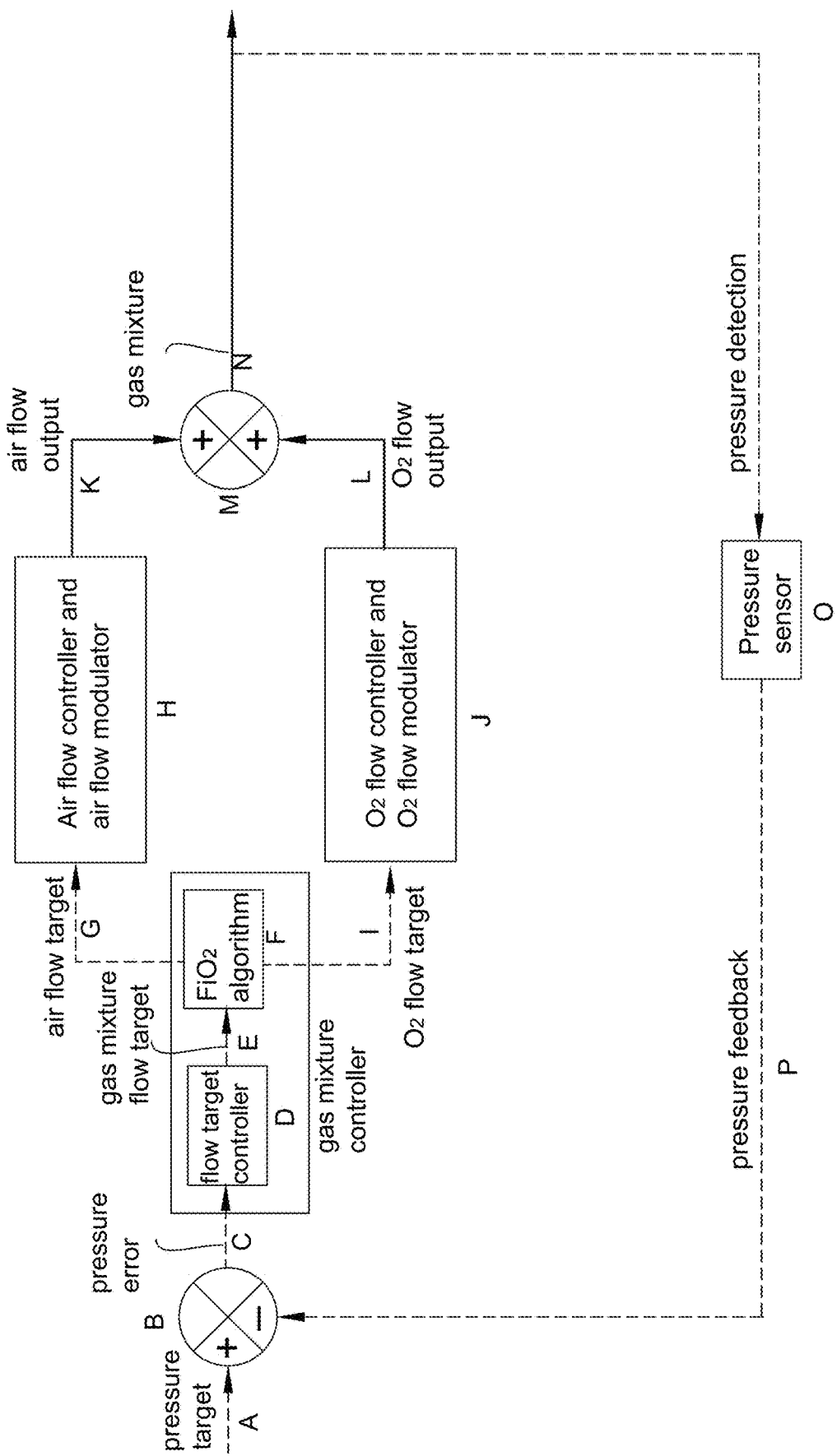
FIG. 5 depicts a pressure feedback control loop used by controller useful in a ventilator of the invention.
Figure 8:
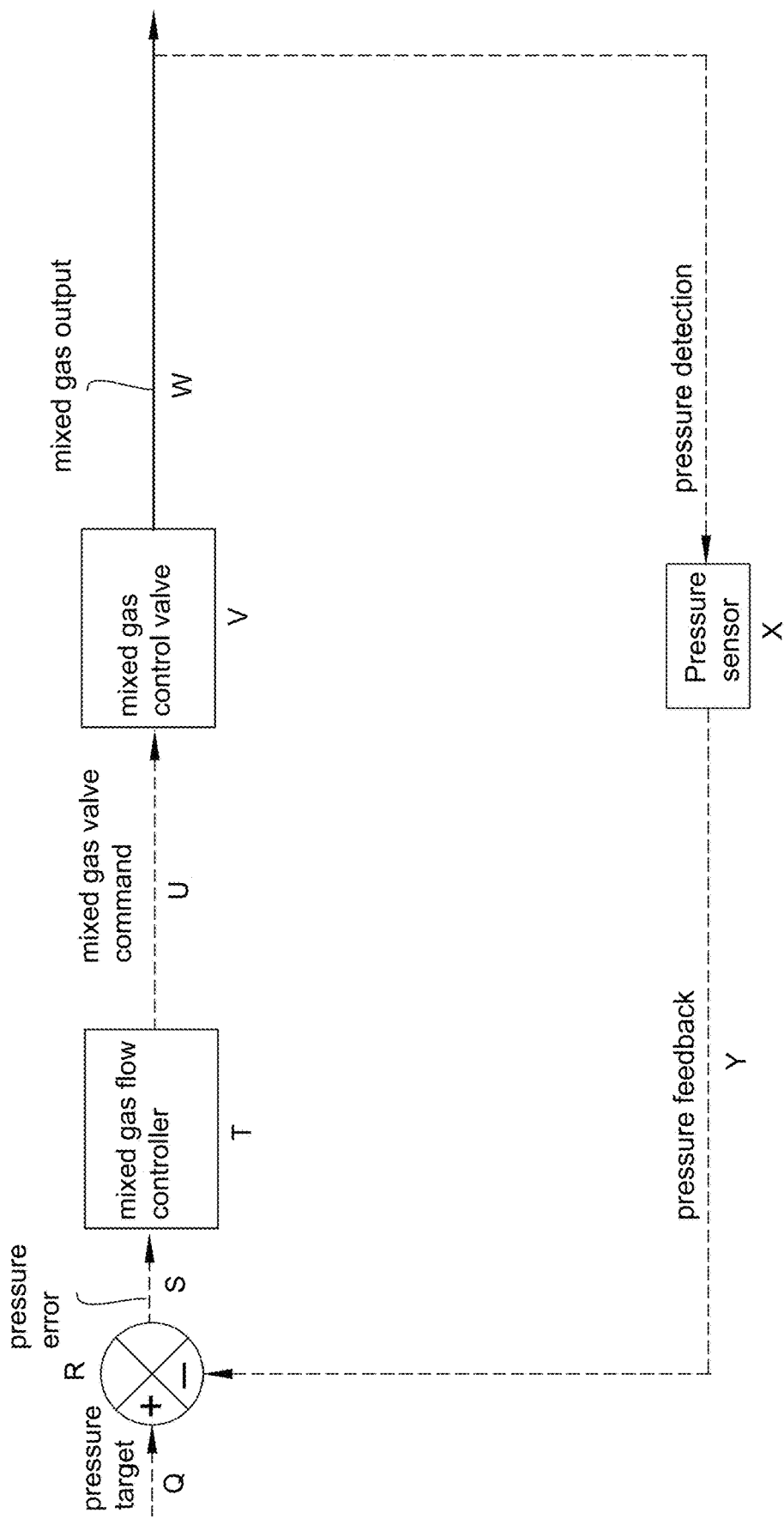
FIG. 8 depicts a feedback control loop used by a controller useful in the present invention.

Optionally, a controller is configured to provide a command. The command can comprise, e.g. a digital command or an analog command. A digital command (e.g. a command comprising a parameter target a target flow, a target volume or a target pressure) can optionally be a command provided (e.g. input in) to an algorithm or another controller that produces one or more commands or outputs based on the digital command. An analog command (e.g. a command comprising a voltage provided to a flow modulator) can optionally be an analog signal provided to one or more flow modulators. As used herein, commands are sometimes referenced by the gas parameter they are configured to target and that is optionally measured as feedback for the controller to correct the command. For example, a pressure feedback loop can be a feedback loop configured to produce a target pressure (e.g. a constant pressure setpoint), e.g. by commanding a flow modulator (e.g. as depicted in FIG. 8). As another example, a pressure feedback loop can be a feedback loop configured to produce a target pressure by commanding a target flow (e.g. as depicted in FIG. 5). As another example, a flow feedback loop can be a feedback loop configured to produce a target flow, e.g. by commanding a flow modulator (e.g. as depicted in FIG. 6A and FIG. 6A).

Optionally, the controller is configured to use a feedback control loop. A feedback control loop can be, e.g., any series of steps comprising at least one step of command by the controller that is configured to produce (e.g. directly or indirectly) a gas exhibiting a parameter target and further comprises at least one step of providing feedback of the output to the controller, wherein the feedback is used by the controller to correct the command, e.g. to more accurately achieve the parameter target in a subsequent step of command. Examples of feedback control loops useful in the invention are depicted in FIG. 5 through FIG. 8, FIG. 10, and FIG. 11.

Optionally, a controller configured to use a feedback control loop is configured to receive a parameter target (e.g. target pressure profile or single target pressure), for example from a user of the ventilator, and provide a setpoint based on the parameter target. For example, the parameter target optionally comprises a parameter profile comprising one or more parameter targets (e.g. pressure targets). Each of the one or more parameter targets can be provided as a setpoint.

For example, the parameter target optionally comprises a pressure profile having a constant pressure and the setpoint provided by the controller is the constant pressure. As another example, the parameter target optionally comprises a pressure profile having a specific pressure shape (e.g. pressure vs time curve) having a desired rise time and the setpoint is a point in the pressure shape. As another example, the parameter target can be a target flow (e.g. target flow profile or flow vs time curve) and the controller can provide one or more flow setpoints. Accordingly, setpoints provided by the controller can change or can remain constant, and can be compared to feedback received from one or more sensors to correct a command (e.g. a command provided to a flow modulator or a command provided to another controller).

Figure 7:
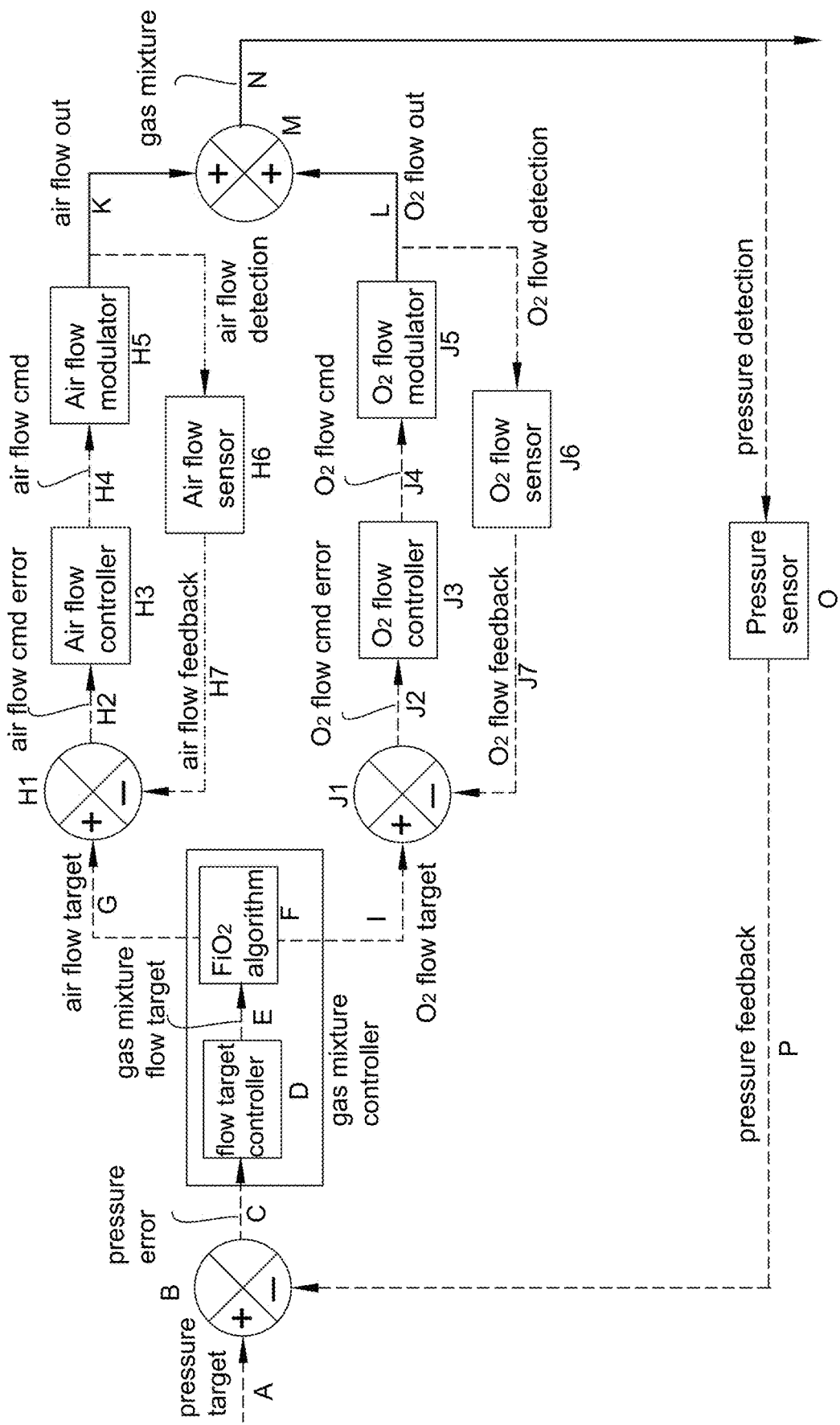
FIG. 7 depicts a feedback control loop used by a controller useful in the present invention.

Optionally, the controller is configured to use a cascaded feedback control loop. Optionally, the cascaded feedback control loop comprises an outer feedback control loop and one or more inner feedback control loops that are within the outer loop. Optionally, the one or more inner feedback control loops comprise a plurality of parallel feedback loops, e.g. as depicted in FIG. 7. For each feedback loop, the controller is optionally configured to provide (e.g. obtain or calculate) a parameter target, provide a command that, when carried out, achieves the parameter target (e.g. an analog signal calibrated to achieve the parameter target using a flow modulator or a digital signal comprising a flow target that, when achieved, achieves the parameter target), obtain the actual value of the gas parameter from a sensor as feedback of the command, compare the actual value to the target to produce a command error (e.g. the difference between the target and the actual value), and modify a subsequent command based on the command error in real time. Optionally, the cascaded feedback loop comprises a pressure feedback loop as an outer loop, an air flow feedback loop as a first inner loop, and an oxygen flow feedback loop as a second inner loop (e.g. as depicted in FIG. 7). Optionally, the pressure loop is configured to achieve a pressure target by commanding a target gas mixture flow, wherein an algorithm is used to provide a target oxygen flow and a target air flow based on the target gas mixture flow and a target oxygen content, and wherein the air flow loop is configured to modulate air flow to achieve the target air flow by commanding an air flow modulator, and wherein the oxygen flow loop is configured to modulate oxygen flow and achieve the target oxygen flow by commanding an oxygen flow modulator. The pressure loop can, e.g. command a target flow of a gas mixture that achieve a target pressure, wherein an algorithm splits the command into a target air flow and a target oxygen flow based on an target oxygen content, e.g. as depicted in FIG. 5. Target air flow is optionally achieved by a controller configured to a use an air flow feedback loop, as depicted in FIG. 6A. Target oxygen flow is optionally achieved by a controller configured to a use an oxygen flow feedback loop, as depicted in FIG. 6B.

Gas Mixture Controller

A controller useful in the present invention can comprise a gas mixture controller configured to provide a command that produces a gas mixture exhibiting at least one parameter target (e.g. one or more of target pressure, target volume, target flow, and target oxygen content). The command can produce the gas mixture directly, e.g. by commanding a flow modulator, or indirectly, e.g. by commanding a target flow of one or more flow controller, that in turn produces the gas mixture. The gas mixture can be, e.g. a mixed gas delivered to a patient interface or a mixing chamber gas. Accordingly, the gas mixture controller can be, e.g. a mixed gas controller or a mixing chamber controller.

Optionally, the controller is configured to provide (e.g. obtain from a user) a target gas mixture pressure and a target gas mixture oxygen content and determine a target gas mixture flow that achieves the target pressure and determine a target air flow and a target oxygen flow that collectively achieves the target gas mixture flow and the target gas mixture oxygen content.

Optionally, the gas mixture controller comprises a gas mixture module configured to:
 a. obtain a target pressure;
 b. obtain a target oxygen content;
 c. determine a mixed gas flow command based on the target pressure and the oxygen content command, wherein the mixed gas flow command comprises a target air flow and a target oxygen flow command;
 d. control an air flow modulator based on the target air flow; and
 e. control an oxygen flow modulator based on the target oxygen flow.

Optionally, the step of controlling an air flow modulator comprises sending the target air flow to an air flow controller. Optionally, the step of controlling an oxygen flow modulator comprises sending the target oxygen flow to an oxygen flow controller. As used herein, the term 'sending', as used in reference to sending of a command from a first controller to a second controller (e.g. an independent second hardware component, a second module of the same controller, or a second subroutine of the same module) includes sending the command from the first controller to the second controller wherein the first and second controllers are separate hardware components, or the first controller making the command available for retrieval by a second controller, e.g. wherein the first and second controllers are modules or subroutines on a single hardware component and the second controller references the command produced by the first controller.

Optionally, the gas mixture module is further configured to perform the following steps following control of the air and oxygen flow modulators:
 a. obtain a pressure reading from a pressure sensor of the gas mixture ('pressure feedback');
 b. compare the pressure feedback to the target pressure;
 c. determine a pressure error based on the comparison of the pressure feedback and the target pressure;
 d. based on the pressure error, correct the mixed gas flow command; and
 e. repeat steps a.-d. a plurality of times (e.g. continuously).

Air Flow Controller

A controller useful in the present invention can comprise an air flow controller configured for controlling an air flow modulator.

Optionally, the air flow controller comprises an air flow module configured to:
 a. obtain a target air flow (e.g. from a gas mixture controller);
 b. provide an air flow command based on the target air flow (e.g. a command that is calibrated to achieve the target air flow);
 c. command the air flow modulator with the air flow command;
 d. determine the actual air flow in the air flow line ('air flow feedback'), e.g. by obtaining an air flow reading from an air flow sensor or by calculating actual air flow based on (e.g. as the difference between) actual gas mixture flow and actual oxygen flow;
 e. compare the air flow feedback to the target air flow;

f. determine an air flow error based on the comparison of the air flow feedback and the target air flow;

g. based on the air flow error, correct the air flow command; and h. repeat steps c.-g. a plurality of times (e.g. continuously).

Figure 1:
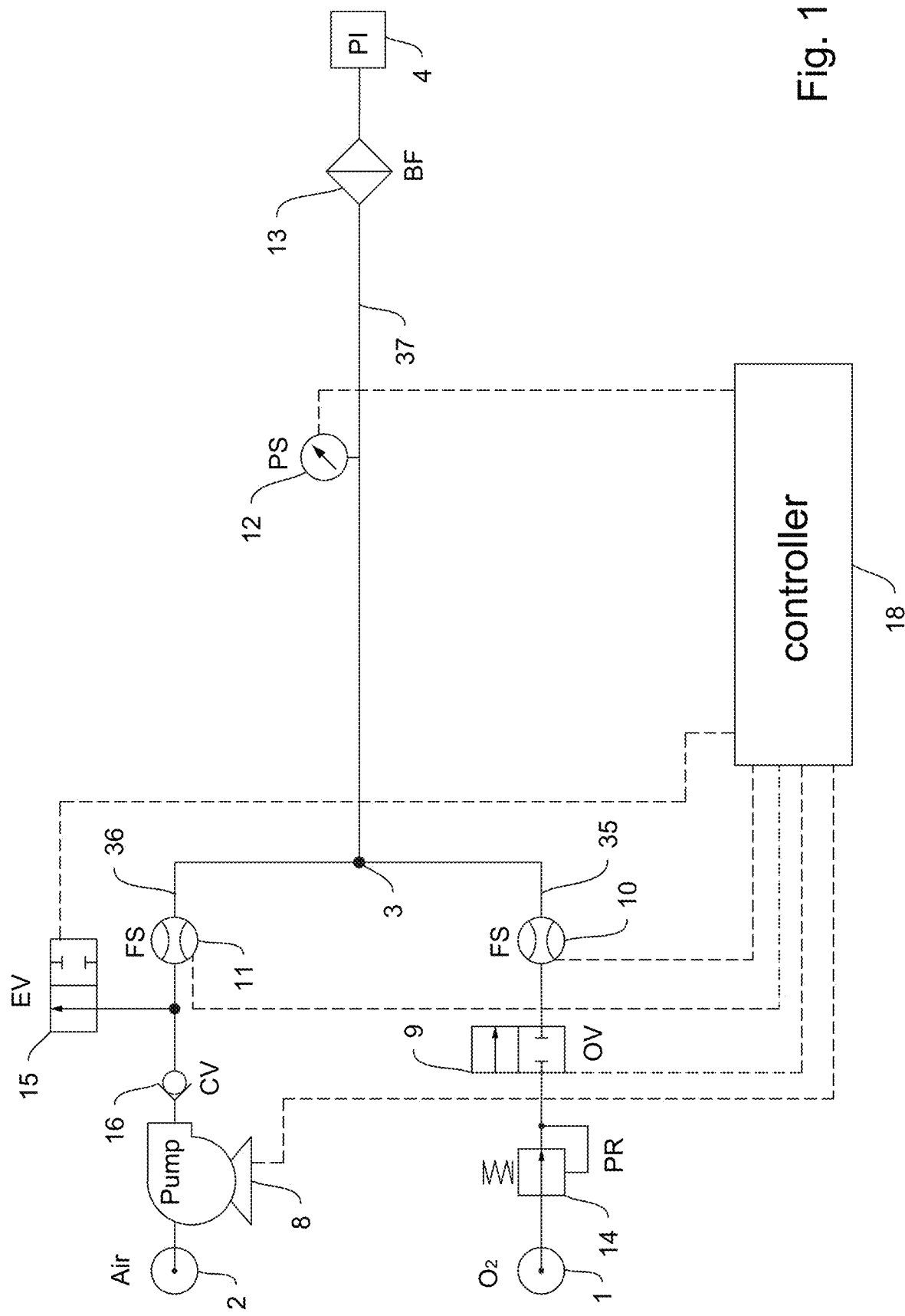
FIG. 1 depicts a ventilator of the invention

Oxygen Flow Controller Embodiment FIG. 1

A controller useful in the present invention can comprise an oxygen flow controller configured for controlling an oxygen flow modulator.

Optionally, the oxygen flow controller comprises an oxygen flow module configured to:

a. obtain a target oxygen flow (e.g. from a gas mixture controller);

b. provide an oxygen flow command based on the target oxygen flow (e.g. a command that is calibrated to achieve the target air flow);

c. command the oxygen flow modulator with the oxygen flow command;

d. determine the actual oxygen flow in the oxygen flow line ('oxygen flow feedback'), e.g. by obtaining an oxygen flow reading from an oxygen flow sensor or by calculating actual oxygen flow based on (e.g. as the difference between) actual gas mixture flow and actual air flow;

e. compare the oxygen flow feedback to the target oxygen flow;

f. determine an oxygen flow error based on the comparison of the oxygen flow feedback and the target oxygen flow;

g. based on the oxygen flow error, correct the oxygen flow command; and h. repeat steps c.-g. a plurality of times (e.g. continuously).

Target Parameters

A controller useful in the present invention can be configured to control an air flow modulator and an oxygen flow modulator to produce a gas mixture exhibiting a plurality of parameter targets. The gas mixture can be, e.g., a mixed gas that flows from a junction fed by an air line and an oxygen line or, as another example, the gas mixture can be a mixing chamber gas fed by an air line and an oxygen line. One or more steps of controlling a modulator or another controller to produce a gas exhibiting a parameter target is also referred to herein as 'achieving' the parameter targets. Parameters that are targeted (e.g. oxygen content, pressure, flow, or volume) are also referred to herein as 'target parameters'. The target (e.g. target value, target profile, or target shape) of such a target parameter is also referred to herein as a 'parameter target'. According to the present invention, the plurality of gas mixture parameter targets comprises a target oxygen content and at least one of a target pressure, a target flow, and a target volume.

Optionally, to achieve a gas mixture parameter target (e.g. target pressure or target flow), the controller determines a parameter target (e.g. target flow) for each of the feed lines. For example, the controller can be configured to determine a target oxygen flow (i.e. target flow of gas through the oxygen line) and a target air flow (i.e. target flow of air through the air line) that produce a gas mixture exhibiting a target oxygen content and at least one of a target pressure, a target flow, and a target volume.

Optionally, the gas mixture is a mixing chamber gas fed by an air line and an oxygen line. In such an embodiment, the target parameters of the mixing chamber gas can optionally comprise oxygen content and pressure. Further, in this embodiment, the controller is optionally configured to achieve a parameter target (e.g. target pressure, target flow, or target volume) of a mixed gas that delivers gas from the mixing chamber to a patient interface, e.g. by modulating a mixed gas control valve.

According to the present invention, a controller can achieve a parameter target by controlling one or more flow modulators. Optionally, the controller is configured to achieve a parameter target by using the parameter target as a feedback control loop target ('setpoint'). For example, the parameter target can comprise a target flow, wherein the controller provides the flow target as a setpoint for controlling a flow modulator. Additionally or alternatively, a controller can optionally be configured to achieve a target of a first parameter by calculating a target for a second parameter, wherein the first parameter is a function of the second parameter. For example, the parameter target can comprises a target pressure, wherein the controller is configured to calculate a target flow as a setpoint, wherein pressure is a function of flow, such that achieving the target flow achieves the target pressure (e.g. upon correction of the target flow). As another example, the parameter target can comprise a total flow such as the target flow of a mixed gas line or sum of target flows of an air line and an oxygen line that feed a mixing chamber, and the controller is configured to calculate the target flow setpoints for a plurality of feed lines (e.g. an oxygen line and an air line), wherein the total flow is the sum of the feed line flows. As another example, the parameter target can comprise a target pressure (e.g. of a mixing chamber gas), and the controller is configured to calculate the target tidal volume setpoints and/or the total volume delivered through a plurality of feed lines. For each parameter setpoint of a feedback control loop, the controller can optionally be configured to receive feedback from a sensor of the respective parameter for comparison with the setpoint.

A parameter target (e.g. target mixed gas parameter) such as target pressure, target volume, or target flow, can optionally be a parameter target value or a parameter target profile. A parameter target profile can include e.g. a parameter target shape, a target change in parameter value, a target rate of change, a target pattern of parameter values, or a parameter target function. For example, a target pressure profile can comprise a target pressure shape having an adjustable rise time setting and/or a gradual pressure profile (e.g. for patient safety or comfort). Optionally, the controller is configured to provide a plurality of alternative pressure shapes (e.g. as choices to a user), e.g. pressure shapes having different rise times such as a first rise time (e.g. fast rise time), a second rise time (e.g. medium rise time), and a third rise time (e.g. slow rise time).

Optionally, the target oxygen content is a target value (e.g. a constant value).

Optionally, the one or more target parameters include any of: tidal volume, respiratory rate, breath time or period, inhalation time or period, exhalation time or period, inhalation volume, peak flow, flow rate, respiration flow curve shape, respiration pressure curve shape. Other useful target parameters are known in the art.

The parameter targets can be fixed or can fluctuate over time. For example, the controller can be configured to provide a breathing regimen in which the one or more parameters of the mixed gas (e.g. pressure) fluctuate over time. Optionally, the breathing regimen comprises a pattern of fluctuations in one or more parameters (e.g. pressure). For example, the breathing regimen can comprise a plurality of phases that alternate, such as an inhalation phase and an exhalation phase. As used herein, the term 'maximum target' (e.g. 'maximum target pressure') refers to the maximum value of a target profile. The term 'instant', when used with respect to a parameter target means the current value of the parameter, e.g. the instant pressure of the mixed gas line is the actual current pressure of the mixed gas line and the instant target pressure is the target value for the instant pressure.

Optionally, the ventilator comprises a mixing chamber, and the controller is configured to provide a mixed gas having a target pressure and a mixing chamber gas having a target pressure, wherein the mixed gas is delivered to a patient, and wherein the target pressure of the mixing chamber is greater than the target pressure of the mixed gas. Optionally, the controller is configured to calculate the target pressure of the mixing chamber gas based on the target pressure of the mixed gas. For example, the controller can comprise an equation that references the target pressure of the mixed gas as an independent variable and the target pressure of the mixing chamber gas as a dependent variable. Optionally, the equation defines a difference (e.g. a set overage) or a ratio between the mixing chamber gas target pressure and the mixed gas target pressure. Optionally, the mixed gas target pressure is a target pressure profile, and the mixing chamber gas target pressure is based on the instantaneous pressure value or the maximum pressure value of the target pressure profile. For example, the mixing chamber target pressure can be a set overage of or a ratio of the instantaneous pressure value or the maximum pressure value of the target pressure profile.

Parameter targets of a gas mixture (e.g. the mixed gas) can be inputted by a user or can be determined (e.g. calculated) based on another parameter target (e.g. which is inputted by a user). For example, a ventilator can optionally be configured to receive an input (e.g. user input) comprising a target pressure and optionally a target volume and/or a target flow. Additionally or alternatively, a ventilator can comprise a flow target controller configured to determine a target flow based on parameter target such as a target pressure or a target volume. Optionally, a target flow determined based on a target volume, wherein the target flow is adjusted based on a real time measurement of volume error.

Other Parameters

Optionally, controller output is dependent on one or more input parameters, e.g. input parameters detected by a sensor. Such parameters can be used, e.g. as triggers for steps of control of flow modulator or steps of controlling an alarm.

Input parameters optionally include physiologic parameters.

The physiological parameters may include one or more of blood pressure, heart rate, pulse oximetry, blood gas level, ECG, EEG, body temperature, (end-tidal) carbon dioxide concentration, parameters indicating pending cardiac conditions, cardiac output, snoring detection, and sedation index.

Ventilation Modes

The ventilator controller of the invention can be configured to provide any mode of ventilation.

Optionally, the ventilator mode comprises a breathing profile and/or a breath cycle. Optionally, the breathing profile comprises an inhalation phase and an exhalation phase.

Optionally, the inhalation phase is patient-triggered or machine-triggered. A patient-trigged inhalation is a spontaneous breath initiated by the subject, wherein the trigger is provided by the patient (e.g. patient breathing effort) and, for example, the controller receives feedback from a sensor that responds to patient breathing effort (e.g. a sensor that detects a change in flow or pressure in ventilator indicative of patient breathing effort). A machine-trigged inhalation is a mandatory breath initiated by the controller, e.g. triggered by the elapsed time following the initiation of previous inhalation and/or exhalation phase.

Optionally, the controller is configured to provide a breath cycle. A breath cycle optionally comprises one or more triggers of cycle events, e.g. inhalation, exhalation, inhalation initiation, inhalation termination, exhalation initiation, and/or exhalation termination. Optionally, the breath cycle comprises an inhalation trigger. Optionally, breath cycle comprises an inhalation initiation trigger, e.g. that includes one or more instructions containing at least one event that initiates an inhalation phase. Optionally, the breath cycle comprises an inhalation termination trigger, e.g. that includes one or more instructions containing at least one event that terminates an inhalation phase.

Optionally, the breath cycle contains an inhalation termination trigger. Optionally, the inhalation termination trigger comprises a target pressure (e.g. mixed gas pressure), target inhalation tidal volume (e.g. mixed gas tidal volume), a target time (e.g. duration of elapsed time following the start of an inhalation phase), or a target flow (e.g. flow rate of mixed gas).

Optionally, the controller is configured for using different cycles and/or triggers for a plurality of breaths. For example, an inhalation phase of a first breath can be terminated based on a target pressure and an inhalation phase of a second breath can be terminated based on a target volume. Optionally, the controller is configured for terminating an inhalation phase based on a target volume, wherein the target volume is adjusted between at least two breaths. For example, the controller can be configured to set a first target volume and adjust the target volume in subsequent breaths upon one or more parameters being met or unmet (e.g. adjusting the target volume to obtain a target pressure).

Optionally, the controller is configured for receiving (e.g. from a user) a trigger definition such as a cycle setpoint, e.g. that triggers one or more events in a breath cycle such as termination of inhalation. Optionally, the controller is configured for receiving an inhalation termination cycle setpoint of a first parameter (e.g. pressure) and an inhalation termination cycle setpoint of a second parameter (e.g. volume) which are used independently or in concert to trigger termination of an inhalation phase of one or more breaths.

Optionally, the controller is configured for providing a mandatory breath, or a spontaneous breath. A mandatory breath can comprises an inhalation phase in which the controller controls the timing, tidal volume or both. A spontaneous breath can be, e.g. an inhalation phase in which the timing and/or the tidal volume is controlled by the patient.

Optionally, the controller is configured to provide any of the following modes of ventilation: mandatory ventilation, spontaneous ventilation, intermittent mandatory ventilation ('IMV'), synchronized intermittent mandatory ventilation ('SIMV'), continuous mandatory ventilation ('CMV'), continuous positive airway pressure ('CPAP'), pressure support ventilation ('PSV'), and continuous spontaneous ventilation ('CSV').

Optionally, the controller is configured to provide any of the following modes of ventilation: Spontaneous, Spontaneous Timed, and Timed. Optionally, any of such ventilation modes is a leak mode.

Optionally, the controller is configured to provide any of the following modes of ventilation: Volume Control Ventilation, Pressure Control Ventilation, Pressure Regulated Volume Control, Volume Support, Proportional Assist Ventilation, and Volume Assured Pressure Support.

Optionally, the controller is configured to provide a flow pattern selected from constant flow (e.g. square wave flow), ascending ramp flow, sine wave flow, descending ramp flow, and decaying exponential flow.

Oxygen

According to the present invention a ventilator comprises an oxygen inlet for receiving pressurized oxygen. The oxygen inlet can optionally be connected to any oxygen source containing oxygen at a concentration substantially greater than that of the air source. Optionally, the oxygen source comprises pure or substantially pure oxygen.

Optionally, the oxygen source is a pressurized tank or an oxygen pipeline (e.g. a hospital's high-pressure oxygen gas network).

Optionally, the oxygen source comprises a pressure regulator or the ventilator comprises a pressure regulator downstream of the oxygen inlet. The optional pressure regulator can be, e.g. any reducing valve configured to provide gas at a set pressure. The pressure regulator can optionally be a manual valve, a control valve, or a fixed orifice (i.e. not modulatable).

Air

According to the present invention a ventilator comprises an air inlet. The air inlet can be connected to any air source. Optionally, the air source is ambient air. For example the air inlet is optionally a port through which ambient air is drawn by the air pump.

Optionally, the ventilator comprises an air filter downstream of the air inlet. Optionally, the air filter is upstream of the junction. Optionally, the air filter is upstream of the air pump.

Gas Pump

A ventilator of the present invention comprises a gas pump downstream of the air inlet. The pump can be any gas pump. Optionally, the speed of the gas pump is controlled by a controller of the ventilator ('variable speed pump').

Optionally, the pump is a positive displacement pump or a dynamic pump. Positive displacement pumps convey gas by displacing the gas. Dynamic pumps convey gas by transferring energy to the gas from a moving object (e.g. an impeller) to create gas velocity. Examples of useful positive displacement pumps include rotary positive displacement pumps and reciprocating positive displacement pumps. Examples of useful dynamic pumps include fan blowers such as centrifugal flow pumps.

Optionally, the pump is a positive flow pump. Optionally, the positive flow pump is a rotary pump selected from a lobe pump (e.g. roots blower), a screw pump, a liquid ring pump, a scroll pump, and a vane pump. Optionally, the positive flow pump is a reciprocating pump selected from a diaphragm pump, a double acting pump, and a single acting pump.

Optionally, the pump is a dynamic pump comprising an impeller ('fan blower'). The fan blower can comprise, e.g. an axial flow impeller or a radial flow impeller. Optionally, the fan blower is a centrifugal pump. Dynamic pumps such as centrifugal pumps have advantages such as providing reduced production cost ventilators, reduced noise, and reduced power consumption compared to positive displacement pumps commonly used in ventilators that provide high pressure air. However, the prior art has generally failed to produce accurate air-oxygen mixing of low pressure air with high pressure oxygen and has typically instead used high pressure positive displacement pumps or, in the case of the Philips Respironics BiPAP Vision, used a complex combination of many components (e.g. an in-line flow restrictor and a pressure regulation valve) and complex algorithms that are difficult to carry out. Accordingly, through insight of the inventor, it is quite remarkable that low pressure ventilators of the present invention can achieve accurate air-oxygen mixing using dynamic pumps with a high pressure oxygen source.

Optionally, the pump is a low pressure pump, e.g. a low pressure dynamic pump. Such a low pressure pump can be any pump configured to pressurize downstream gas to a pressure of no more than 140 mbar (e.g. no more than 110 mbar or no more than 70 mbar). For example, the design of the pump itself can be configured or rated for providing no more than a maximum pressure (e.g. 140 mbar) or the ventilator controller can be configured to control the pump speed such that the pump produces no more than a maximum pressure (e.g. 140 mbar). Surprisingly, through insight of the inventor, embodiments of the present invention are believed to achieve accurate air-oxygen mixing of low pressure air even with high pressure oxygen (e.g. oxygen from an oxygen tank or hospital oxygen line). This is a remarkable improvement over prior art configurations.

Optionally, the dynamic pump is configured for conveying gas at about 100 liters per minute ('lpm') or greater, e.g. at least about 150 lpm.

Optionally, the pump is a small dynamic pump. A small dynamic pump can be, e.g. a dynamic pump having an impeller diameter of less than about 20 cm, e.g. less than about 18 cm, less than about 14 cm, less than about 10 cm, about 4 cm to about 9 cm, or about 4 cm to about 10 cm. Optionally, the small dynamic pump is a pump configured for conveying gas at no more than 200 lpm. Optionally, the small dynamic pump is a pump configure to produce a gas pressure of no more than about 110 millibar ('mbar), e.g. no more than about 80 mbar or no more than about 60 millibar. Such small dynamic pumps can provide advantages such as, e.g., increased efficiency, and/or reduced size to provide a more compact ventilator while producing accurate flow rates in ventilators of the present invention. Optionally, a small pump comprises a noise reduction mechanism such as noise insulating enclosure. These advantages can be compounded with accurate air/oxygen mixing and pressure targeting using ventilator configurations taught herein.

Conduits

A ventilator of the invention comprises a plurality of conduits that transport gas from the inlets to the patient interface. The ventilator comprises at least a first conduit that conveys gas from the oxygen inlet to a junction ('oxygen line'), a second conduit that conveys gas from the air inlet to the junction ('air line'), and a third conduit that conveys gas from the junction to the patient interface ('mixed gas line').

Oxygen/Air Mixing

A ventilator of the present invention comprises a junction downstream of the air inlet and oxygen inlets. The junction is configured for receiving air from the air line, receiving oxygen from the oxygen line, and outputting a mixed gas to the mixed gas line.

The junction can comprise, e.g. a direct mixing junction or a mixing chamber.

Direct Mixing

A ventilator of the present invention can optionally comprise a direct mixing junction. A direct mixing junction can optionally be any junction which experiences the same pressure as the gas flowing through the patient interface, i.e. does not comprise a reservoir having an over pressure relative to the mixed gas line. Optionally, the direct junction is a passive junction such as a T-junction. Optionally, the direct junction is fixed volume junction. Optionally, the direct junction comprises no moving parts.

Mixing Chamber

A ventilator of the present invention can optionally comprise a mixing chamber. According to the present invention, a mixing chamber is any chamber that is pressurized greater than that of the mixed gas line (i.e. the target pressure of the inspiration gas). In this embodiment, the ventilator comprises a control valve (e.g. proportional valve) downstream of the mixing chamber ('mixed gas control valve'), wherein the mixed gas control valve is controlled by the controller.

Optionally, the mixing chamber comprises a fixed volume reservoir (e.g. a pressurized gas tank). Unlike a piston or bellows mixing chamber or other variable volume mixing chamber, the volume of a fixed volume reservoir does not change as it is filled. Instead, the mixing chamber is pressurized as it is filled.

Optionally, the mixing chamber is a passive reservoir. A passive reservoir is a reservoir that has no luminal moving parts that act to draw in or homogenize gas.

Optionally, the mixing chamber (e.g. fixed volume and/or passive mixing chamber) comprises a volume of at least about 300 ml, e.g. a volume of about 300 ml to about 5000 ml. Optionally, the volume of the mixing chamber (e.g. fixed volume and/or passive mixing chamber) is about 1000 ml to about 3000 ml, e.g. about 1500 ml to about 2500 ml. Such a mixing chamber is useful, e.g. for human subjects. Optionally, the volume of the mixing chamber (e.g. fixed volume and/or passive mixing chamber) is about 300 ml to about 1000 ml. Such a mixing chamber is useful, e.g. for subjects having lung capacities substantially less than adult humans (e.g. infants, children, or veterinary subjects).

Optionally, the mixing chamber comprises a pressure sensor.

Optionally, the controller is configured to pressurize the mixing chamber to a pressure (e.g. instant pressure) greater than that of the mixed gas line (e.g. greater than the instant target pressure or the maximum target pressure of the mixed gas line). Optionally, the controller is configured to pressurize the mixing chamber to a pressure (e.g. instant pressure) at least about 5 mbar (e.g. at least about 10 mbar) greater than that of the mixed gas line (e.g. greater than the instant target pressure or the maximum target pressure of the mixed gas line). Optionally, the controller is configured to pressurize the mixing chamber to a pressure (e.g. instant pressure) about 1 mbar to about 30 mbar (e.g. 5 mbar to about 20 mbar or about 10 mbar to about 20 mbar) greater than that of the mixed gas line (e.g. greater than the instant target pressure or the maximum target pressure of the mixed gas line). Optionally, the controller is configured to pressurize the mixing chamber to a pressure of about 10 mbar greater than the instant pressure of the mixed gas line or greater than the maximum pressure experienced by the mixed gas line. For example, the controller can be configured to pressurize the mixing chamber to a pressure that is about 10 mbar greater than the instant target pressure of the mixed gas or above the maximum target pressure of the mixed gas.

Optionally, the controller is configured to pressurize the mixing chamber to a pressure of less than about 150 mbar, e.g. less than about 100 mbar. Optionally, the controller is configured to limit the pressure of the mixing chamber at all times to less than about 150 mbar. Such a configuration provides enhances safety for the patient and reduces the burden on a pump.

Optionally, the mixing chamber comprises an oxygen sensor.

Optionally, each of the air line and the oxygen line that feed the mixing chamber optionally comprise a flow sensor, i.e. an air flow sensor and an oxygen flow sensor, respectively. Optionally, the controller is configured to control the flow of at least one of air through the air line and oxygen through the oxygen line.

Optionally, the mixed gas line fed by the mixing chamber comprises a mixed gas flow sensor, a pressure sensor, or both.

Optionally, the ventilator comprises an exhalation valve downstream of the mixing chamber and upstream of the patient interface (e.g. upstream of the mixed gas control valve), wherein the exhalation valve is controlled by the controller; and optionally the ventilator further comprises a check valve downstream of the mixing chamber and upstream of the exhalation valve.

Optionally, the oxygen line that feeds the mixing chamber comprises a check valve (e.g. downstream of the oxygen control valve) and/or the air line that feeds the mixing chamber comprises a check valve (e.g. downstream of the pump). Such check valves can be configured to prevent escape of gas from the mixing chamber to the upstream (e.g. upon pressurization of the mixing chamber).

Optionally, the pump that conveys air to the mixing chamber is a variable speed pump or the air line comprises a control valve downstream of the pump (e.g. a constant speed pump).

Through insight of the inventor, a ventilator comprising a mixing chamber as taught herein, can deliver flow/volume and pressure to the patient with high accuracy with uniform oxygen mixing throughout the breath delivery.

Another optional advantage of a ventilator comprising a mixing chamber as taught herein, is that a modular ventilator configuration, e.g. with a disconnectable oxygen line, can be easily designed and implemented and optionally facilitates burden-free servicing.

Sensors

A ventilator of the present invention comprises a plurality of sensors from which the controller receives feedback. Such feedback can optionally be used in the control of flow modulators. The ventilator optionally comprises at least one pressure sensor comprised by the mixed gas line ('mixed gas pressure sensor'), at least a first flow sensor and a second flow sensor. The first and second flow sensors are respectively comprised by two lines selected from an air line, an oxygen line, and a line that transmits a gas mixture of both oxygen from the oxygen line and air from the air line. For example, the first flow sensor can be a flow sensor comprised by the oxygen line ('oxygen flow sensor') and the second flow sensor can be a flow sensor comprised by the air line ('air flow sensor') or a flow sensor comprised by the mixed gas line ('mixed gas flow sensor').

Optionally, the ventilator comprises at least three flow sensors—an oxygen flow sensor, an air flow sensor, and mixed gas flow sensor.

Optionally, the ventilator comprises a mixing chamber and at least two pressure sensors—a first pressure sensor comprised by the mixed gas line and a second pressure sensor comprised by the mixing chamber.

Optionally, the ventilator comprises a sensor of oxygen content ('oxygen sensor'). For example, the ventilator optionally comprises a mixing chamber comprising an oxygen sensor.

Sensors useful in the present invention optionally produce a signal (e.g. digital or analog signal) that can be interpreted by the controller to determine the state or value of sensed parameter.

Sensors comprised by a component of the intention (e.g. conduit) can optionally be placed directly in the component or placed in a bleed line that takes a sample from the component.

Pressure Sensors

Pressure sensors useful in the present invention include any device (e.g. a single device or a collection of devices) capable of producing a signal indicative of the gas pressure and providing the signal to the controller. For example the pressure sensor can be a transducer that converts pressure into an electrical signal (e.g. a strain-gage base transducer).

Optionally, the mixed gas line comprises a pressure sensor. Such a pressure sensor can be used, e.g. to inform the controller of the pressure of the mixed gas that will be delivered to the patient.

Optionally, the ventilator comprises a mixing chamber and the mixing chamber comprises a pressure sensor. Such a pressure sensor can be used, e.g. to inform the controller of the mixing chamber pressure. Optionally, the mixed gas line comprises a proportional valve and the controller compares the actual mixing chamber pressure to a target mixed gas pressure to determine the level of modulation of the proportional valve to achieve the target mixed gas pressure in a mixed gas that is delivered to the patient.

A useful pressure sensor is, for example, a differential pressure sensor.

Oxygen Sensor

A ventilator of the invention optionally comprises an oxygen sensor. Oxygen sensors useful in the present invention include any device capable of producing a signal indicative of the oxygen content of a gas and providing the signal to the controller. For example, the oxygen sensor can produce a signal that converts the concentration of oxygen into an electrical signal, e.g. from which the controller can determine the percentage or fraction of oxygen ('FiO$_2$').

Optionally, the ventilator comprises an oxygen sensor comprised by the mixed gas line or the junction. Such an oxygen sensor can be used, e.g. to inform the controller of the oxygen content of the gas mixture that will be delivered to the patient.

Optionally, the invention contemplates embodiments that compare the oxygen content of the gas mixture to the target gas mixture oxygen content and modulate the oxygen modulator and/or the air modulator to modulate the oxygen content of the mixed gas. While oxygen sensors can optionally be comprised by ventilators of the present invention, certain embodiments taught herein comprise a controller that use flow sensors to provide feedback to oxygen and air modulators and thus can control oxygen content independent of direct measurement of oxygen content for feedback control. Accordingly, even in embodiments wherein an oxygen sensor is comprised by the ventilator, the oxygen sensor can optionally be configured for monitoring purposes (e.g. for display to a user or to trigger an alarm) such that feedback control of oxygen and air modulators and can continue in the event of oxygen sensor malfunction. Additionally or alternatively, the oxygen sensor can be configured as a secondary feedback mechanism in the event that one of the flow sensors malfunction such that the controller uses the oxygen sensor for feedback control of the oxygen and air modulators instead of the malfunctioned flow sensor. Through insight of the inventor, such configurations provide a superior safety feature that ensures accurate delivery of a desired air-oxygen mix.

Optionally, the oxygen sensor is an O$_2$ cell.

Optionally, the ventilator is configured such that the oxygen sensor can be removed and/or installed from the exterior of the ventilator or oxygen line thereof. Additionally or alternatively, the ventilator is optionally configured such that the oxygen sensor can be removed and/or installed without substantially disassembling or opening the oxygen line. For example, the ventilator or oxygen line thereof can be provided with a port (e.g. a tapped hole in a sidewall of the line) which accepts an oxygen sensor, wherein the port is accessible from the outside the ventilator or oxygen line thereof Flow Sensors A ventilator of the invention comprises a plurality of flow sensors. Flow sensors useful in the present invention include any device capable of producing a signal indicative of the flow of a gas and providing the signal to the controller. For example, a flow sensor can comprise a pneumotach, a variable orifice transducer, a mass flow sensor or any flow transducer that produces a signal, e.g. from which the controller can determine the flow rate or instantaneous volume delivered through a conduit.

Optionally, a ventilator has a flow sensor comprised any of the oxygen line, the air line, and the mixed gas line.

Optionally, the ventilator comprises a flow sensor comprised by the mixed gas line. Optionally, such a flow sensor is used to provide feedback for a controller, wherein the controller is configured for a volume- or flow-targeted mode of delivery. Additionally or alternatively, such a flow sensor is optionally used by a controller for measurement of tidal volume, leak (e.g. estimated or calculated leak), flow for breath trigger, or flow for cycling between inhalation and exhalation phases.

Optionally, the oxygen line comprises a flow sensor. Optionally, the flow sensor is downstream of an oxygen control valve. Such placement of the flow sensor downstream of the control valve can, e.g. prevent damage the oxygen flow sensor under fault conditions.

Valves

A ventilator of the invention comprises a plurality of valves.

Valves useful of the present invention include valves configured for modulation by the controller ('control valves') and valves that are modulated by another means ('non-control valves'). Useful non-control valves include manual valves and non-adjustable valves.

Optionally, any valve taught herein can be configured as a control valve. Alternatively, the ventilator comprises a plurality of control valves and at least one non-control valve (e.g. a non-control check valve).

Useful control valves include on-off valves and proportional valves.

Control Valves

Useful control valves include any valve that can be modulated by the controller.

Examples of useful control valves include on-off valves and proportional valves.

Optionally, a valve used in the invention is a fail-safe valve. Fail-safe valves are valves that automatically assume a resting state upon removal of an actuating signal. For example, a fail-safe valve can be a normally closed valve having a resting state in the closed position and which opens upon receiving an open signal from the controller or can be a normally open valve having a resting state in the open position and which closes upon receiving a close signal from the controller.

Ventilators of the present invention comprise at least a first control valve comprised by the oxygen line ('oxygen control valve').

Optionally, the ventilator comprises an exhalation valve as a control valve.

Optionally, one or more of the air line and the mixed gas line comprise a control valve.

Optionally, the oxygen control valve is a proportional valve or an on-off valve.

Optionally, the oxygen control valve is a solenoid, e.g. a proportional solenoid or an on-off solenoid (e.g. a rapid an-off solenoid controlled via pulse width modulation).

Oxygen Control Valve

A ventilator of the present invention can comprise an oxygen control valve. The oxygen control valve can be any control valve comprised by the oxygen line upstream of the junction that can be controlled to modulate the flow of oxygen from the oxygen inlet to the junction. By controlling the oxygen control valve, the controller can modulate parameters of the mixed gas such as the oxygen content and/or pressure.

Optionally, the oxygen control valve is a proportional valve. Alternatively, the oxygen control valve can optionally be an on-off valve, e.g. in embodiments wherein the junction comprises a mixing chamber.

Air Control Valve

Optionally, a ventilator of the present invention comprises an air control valve. The air control valve can be any control valve comprised by the air line upstream of the junction that can be controlled to modulate the flow of air from the air inlet to the junction. By controlling the air control valve, the controller can modulate parameters of the mixed gas such as the oxygen content and/or pressure.

Optionally, the air control valve is a proportional valve. Alternatively, the air control valve can optionally be an on-off valve (e.g. controlled via pulse width modulation), e.g. when the junction comprises a mixing chamber.

Mixed Gas Control Valve

Optionally, a ventilator of the present invention comprises a mixed gas control valve, e.g. in embodiments wherein the junction comprises a mixing chamber. The mixed gas control valve can be any control valve comprised by the mixed gas line downstream of the junction that can be controlled to modulate the flow of mixed gas from the junction to the patient. By controlling the mixed gas control valve, the controller can modulate parameters of the mixed gas such as the pressure or flow.

Optionally, the mixed gas control valve is a proportional valve (e.g. proportional solenoid).

Exhalation Valve

Optionally, a ventilator of the invention comprises an exhalation valve as a control valve. An exhalation valve can optionally be any valve which is opened during an exhalation phase and relatively closed (e.g. completely closed or partly closed) during an inhalation phase.

Optionally, the exhalation valve is an on-off valve.

Optionally, the exhalation valve is a proportional valve (e.g. proportional solenoid or proportional scissor valve). Such a configuration can be used, for example, to add functionality to the ventilator during exhalation and/or inspiration. For example, the proportional exhalation valve can be used to control the amount of back pressure (i.e. through valve orifice size) during exhalation or toggle pressure during inspiration. Optionally, the ventilator comprising such an exhalation valve is configured to provide Airway Pressure Release Ventilation ('APRV')

Optionally, the exhalation valve is a normally open valve which is closed by the controller during an inhalation phase. In this configuration, patients can breathe freely from room air in case of power failure or machine failure. Alternatively, the exhalation valve can be a normally closed valve which is opened by the controller during an exhalation valve. Alternatively, the exhalation valve can receive an open signal from the controller during the exhalation phase and receive a close signal from the controller during the inhalation phase.

In embodiments comprising an exhalation valve, the ventilator optionally comprises a valve upstream of the exhalation valve that prevents gas from flowing upstream ('exhalation isolator') to one or more components such as a blower or a mixing chamber. The exhalation isolator can be a control valve or non-control valve. As an illustrative example, the exhalation isolator can comprise a check valve upstream of the exhalation valve. As another example, the exhalation isolator can be a control valve that is closed during an exhalation phase. A check a valve is used as an illustrative example of an exhalation isolator. However, for each of said examples, the invention also provides an alternative embodiment comprising any exhalation isolator.

Optionally, the ventilator comprises the exhalation valve upstream of a flow sensor. In this configuration, the controller can measure the exhaled gas, e.g. in a single limb patient circuit configuration using a flow sensor that is configured to measure both inhaled gas and the exhaled gas. The measurement of exhaled gas can be used by the controller, e.g. to perform any of the following: measure exhalation flow, determine exhalation tidal volume, determine duration of exhalation phase, and determine the cycle time to switch from an exhalation phase to an inhalation phase.

Optionally, the exhalation valve and the exhalation isolator can be independent valves that collectively achieve the desired function, e.g. an exhalation valve and check valve positioned next to each other or separated by other components such as conduits and valves). Alternatively, the exhalation valve and the exhalation isolator can optionally be subcomponents of a single valve, for example, a three way valve with an exhaust port.

Optionally the ventilator comprises a valve having exhalation valve and exhalation isolator functions. For example, a three way valve can be provided which has an inlet port which receives an inlet flow of gas from upstream, an outlet port which outflows gas downstream towards the patient, and an exhaust port configured for exhausting downstream air. Such a three-way valve can optionally be a normally closed valve which, when unactuated, blocks inlet flow and connects the outlet port to the exhaust port, and which, when actuated by the controller, connects the inlet port to the outlet port and blocks the exhaust port. Alternatively, such a three-way valve can optionally be a normally closed valve which, when unactuated, passes inlet flow from the inlet port to the outlet port and blocks the exhaust port, and which, when actuated by the controller, blocks the inlet flow and connects the outlet port to the exhaust port.

Among the other advantages taught herein, a ventilator having an exhalation valve and isolation valve, e.g. in a single limb ventilator, can isolate the patient interface, reducing the chances of cross-contamination of upstream components during exhalation.

One advantage of an exhalation valve as taught herein is that it can optionally be configure to prevent potential cross contamination of the components. This allows, e.g. the ventilator to be used by one or more additional patients after a first patient has used the ventilator. While a bacteria filter is optionally provided, e.g. upstream of a patient interface, the exhalation valve can configured to protect upstream components from cross-contamination in embodiments that do not comprise a bacteria filter. For example, while a ventilator of the invention can be manufactured that has a connector at the furthest downstream end of the mixed gas line configured for connection to patient interface and optionally connected to a bacteria filter between the connector and the patient interface. While the manufacture may optionally recommend the use of a bacteria filter at the ventilator outlet, this is not always practiced by users a cost-effective and simple solution would eliminate concerns from clinicians, equipment providers/dealers, care givers and patients as well. Through insight of the inventor, employing an exhalation valve optionally configured as taught herein, a potentially very serious issue of cross-contamination can be eliminated at minimal cost and burden to users.

Check Valves

A ventilator of the invention optionally comprises one or more check valves that prevent the transmission of gas from downstream to upstream.

Optionally, the ventilator comprises at least one check valve upstream of an exhalation valve and downstream of a blower.

Optionally, the ventilator comprises at least one check valve upstream of an exhalation valve and downstream of a mixing chamber.

Optionally, the ventilator comprises at least one check valve upstream of a mixing chamber and downstream of the blower.

Optionally, the ventilator comprises at least one check valve upstream of a mixing chamber and downstream of an air inlet.

Optionally, the ventilator comprises at least one check valve upstream of a mixing chamber and downstream of an oxygen inlet.

Optionally, the ventilator comprises at least one check valve upstream of the junction and downstream of the air inlet.

Optionally, the ventilator comprises at least one check valve upstream of the blower and downstream of the air inlet.

Pressure Regulator

Optionally, a ventilator of the invention comprises a pressure regulator downstream of the oxygen inlet, e.g. upstream of the oxygen control valve. The pressure regulator can be, e.g. any reducing valve configured to provide gas at a set pressure. The pressure regulator can optionally be a manual valve, a control valve, or a fixed valve (i.e. not modulatable).

Proportional Valves

A ventilator of the invention comprises at least one proportional valve. According to the present invention, a proportional valve is any valve that can be modulated by the controller to assume a first position, a second position, and a plurality of positions intermediate of the first and second positions. Optionally, the first position is fully open. Optionally, the second position is fully closed. Optionally, the plurality of intermediate positions vary from each other by less than 10% (e.g. less than 5%, less than 1%, less than 0.5%, or are continuously variable) which respect to orifice or flow rate.

Optionally, a proportional valve is a continuously variable valve (e.g. with an infinite number of intermediate positions) or a discrete position valve (e.g. with a discrete number of intermediate positions).

Optionally, the proportional valve is a continuously variable valve having less than 3% of center overlap. Alternatively, the proportional valve is optionally a continuously variable valve is any variable valve having a center overlap of at least 3%.

Optionally, the proportional valve is a solenoid valve or a stepper valve.

Optionally, the proportional valve is a solenoid valve such as a stroke-controlled solenoid or a force-controlled solenoid.

Optionally, the proportional valve comprises a servo motor.

Optionally, the proportional valve is a plunger valve or a butterfly valve.

Patient Interface

A ventilator of the present invention can optionally comprise a patient interface or can be configured for connection to a patient interface (e.g. the ventilator comprises a tube coupler downstream of the junction). Useful patient interfaces include any component configured to deliver the mixed gas to the lungs of a subject.

Optionally, the patient interface comprises a mask, a mouth piece, a nasal prong, or a tube.

Optionally, the patient interface comprises a tube, e.g. a tube that is inserted into the patient. Optionally, the tube comprises a tracheal tube, e.g. an endotracheal tube, a tracheostomy tube, or a tracheal button.

While the invention is frequently illustrated herein as a ventilator comprising a patient interface and an optional bacteria filter, the invention also provides, for each of said embodiments, an alternative embodiment that comprises a connector on the mixed gas line (e.g. at the outlet or most downstream end), e.g. rather than comprising a patient interface or optional bacteria filter. The connector can be configured, e.g. for connection to a patient interface (or a gas conduit) and optionally a bacteria filter. Such a configuration allows the user to obtain a ventilator of the invention and independently obtain a patient interface, e.g. a generic patient interface of his choice from any manufacturer.

Modular Ventilator

A ventilator of the present invention can optionally be configured such that the oxygen line can be disconnected from the ventilator, e.g. at the junction. In such a configuration, two independent systems can be provided. For example, a first system can be provided having an air line, a mixed gas line, and a junction comprising a connector configured for coupling to an oxygen line such that the junction mixes oxygen and air when the oxygen line is connected. A second system can be provided having an oxygen line configured for connection to the junction. Controlled components of the oxygen line (e.g. an oxygen valve and oxygen sensor) can be configured for coupling (e.g. via a data link) to the first controller for control thereby or, alternatively, the second system can comprise a second controller configured for coupling (e.g. via data a link) to the first controller.

Among other advantages, such a ventilator allows patients who do not require additional oxygen to use or purchase a ventilator having only the air system, reducing the cost of the devices. If and when oxygen mixing is needed, the oxygen system can be added to the existing system, enabling the ventilator to be upgraded without purchasing a replacement ventilator. Accordingly, the oxygen system can be implemented internally or installed as an external add-on module, thus allowing various options of devices.

Other Gases

While the invention has been illustrated by using air and oxygen as gas sources, the invention contemplates ventilators configured to mix any gases. For example, the invention contemplates a ventilator configured to use a first gas and a second gas in place of the air and the oxygen, respectively. Accordingly, it is to be understood that, in such embodiments, the components of the respective feed lines, which are often referred to herein as 'air' components or 'oxygen' components (e.g. air flow sensor, oxygen flow sensor, oxygen control valve, etc.) can instead be referred to 'first gas' components or 'second gas' components, respectively (e.g. first gas flow sensor, second gas flow sensor, second gas control valve, etc. The first gas and second gas can optionally each be selected from air, oxygen, a noble gas (e.g. xenon), an anesthetic, nitrogen, or a gas mixture comprising any of said gases and one or more additional gases. Optionally, the first gas is air (e.g. ambient air) and the second gas is any gas, e.g. an auxiliary gas (e.g. pressurized gas) such as oxygen, a noble gas (e.g. xenon), an anesthetic, or nitrogen. Additionally, a ventilator of the invention can be configured to mix three or more gasses (e.g. a third gas in addition to the first and the second gases).

EXAMPLES

Example 1 Ventilator

One embodiment of the invention provides a ventilator having a pump upstream of an air/oxygen junction. An example of such a ventilator is depicted in FIG. 1

The ventilator comprises an oxygen inlet 1, an air inlet 2, a junction 3 downstream of the inlets 1,2 and a patient interface 4 downstream of the junction 3. Oxygen is conveyed through oxygen line 35, which is a gas conduit, from the oxygen inlet 1 to the junction 3. Air is conveyed through air line 36, which is a gas conduit, from the air inlet 2 to the junction 3. Air and oxygen are mixed at the junction 3 to form a mixed gas which is conveyed from the junction 3 to the patient interface by mixed gas line 37, which is a gas conduit. The junction can be, e.g. a passive junction such as a T-junction.

The oxygen line 35 comprises an oxygen control valve 9, which is a proportional valve such as a proportional solenoid. The oxygen control valve 9 is positioned downstream of the oxygen inlet 1 and upstream of the junction 3 to modulate the flow of oxygen from the oxygen inlet 1 to the junction 3. The oxygen line 35 also comprises an oxygen flow sensor 10, e.g. downstream of the oxygen control valve 9, which measures the flow of gas through the oxygen line 35. Optionally, the ventilator comprises a pressure regulator 14, e.g. if the oxygen inlet 1 is connected to an unregulated source of oxygen.

The air line 36 comprises a pump 8 downstream of the air inlet 2 and upstream junction 3, which pumps gas from the air inlet 2 to the junction 3. The pump 8 is optionally a variable speed pump such as a variable speed blower (e.g. a fan blower) that can be modulated by a controller to control the flow of air from the air inlet 2 to the junction 3. As an alternative to a variable speed pump, the ventilator can comprise a control valve (not shown) downstream of the pump and upstream of the junction which is modulated by a controller to control the air flow. The air line 36 also comprises a flow sensor, such as air flow sensor 11 which measures the flow of gas through the air line 36.

The mixed gas line 37 comprises a pressure sensor, such as mixed gas pressure sensor 12, which measures the pressure of the mixed gas in the mixed gas line 37. Optionally, the mixed gas line comprises an air filter such as bacteria filter 13 which filters mixed gas before reaching the patient interface 4.

Optionally, the ventilator comprises a valve, such as exhalation valve 15, which opens to exhaust gas from the ventilator during an exhalation phase and is closed during an inhalation phase. The exhalation valve 15 can be comprised by, e.g. the air line 36 downstream of the pump 8. Upstream of the exhalation valve 15, e.g. downstream of the pump 8, the air line optionally comprises a check valve 16. Such a check valve can be used, e.g. to prevent exhalation gas from the patient from backflowing through cross-contaminating the pump 8 or other upstream components. The exhalation valve 15 can optionally be a normally-open valve (e.g. solenoid) to allow free breathing by the patient in case of ventilator malfunction.

The ventilator further comprises a controller 18 which modulates the oxygen control valve 9 and the pump 8 to control parameters of the mixed gas such as oxygen content and pressure. The controller is configured to obtain feedback from the oxygen flow sensor 10, the air flow sensor 11, and the pressure sensor 12 to correct its modulation of the oxygen control valve 9 and the pump 8 and accurately impart the desired parameters of the mixed gas. Optionally, the controller is configured to modulate an exhalation valve 15 such that the exhalation valve 15 is open during an exhalation phase and is relatively closed during an inhalation phase.

Example 2 Ventilator with Pump Downstream of Junction

Figure 2:
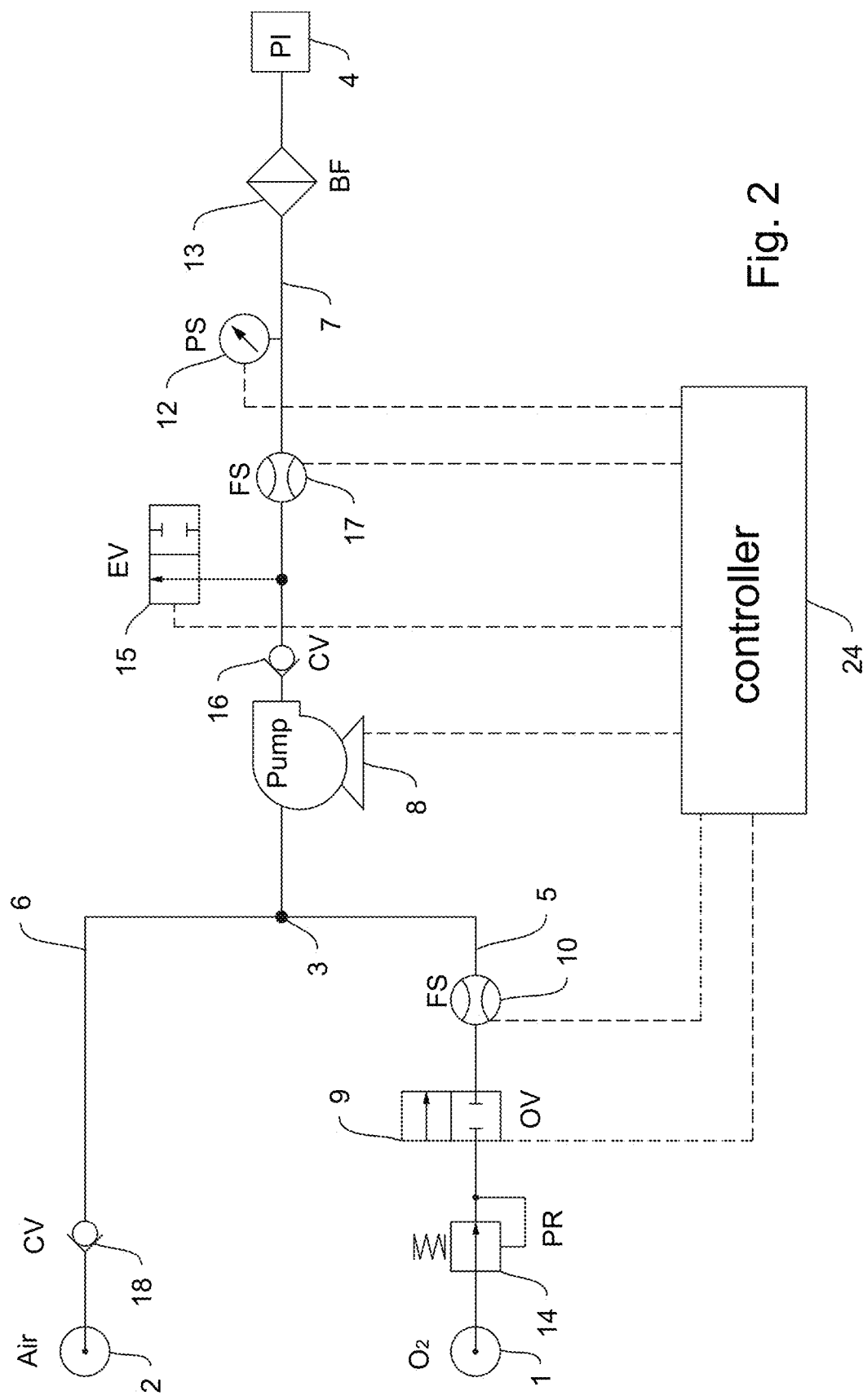
FIG. 2 depicts a ventilator of the invention.

One embodiment of the invention provides a ventilator having a pump downstream of an air/oxygen junction. An example of such a ventilator is depicted in FIG. 2.

The ventilator comprises an oxygen inlet 1, an air inlet 2, a junction 3 downstream of the inlets 1,2 and a patient interface 4 downstream of the junction 3. Oxygen is conveyed through oxygen line 5, which is a gas conduit, from the oxygen inlet 1 to the junction 3. Air is conveyed through air line 6, which is a gas conduit, from the air inlet 2 to the junction 3. Air and oxygen are mixed at the junction 3 to form a mixed gas which is conveyed from the junction 3 to the patient interface by mixed gas line 7, which is a gas conduit. The junction can be, e.g. a passive junction such as a T-junction.

The mixed gas line 7 comprises a pump 8 downstream of the junction 3, which pumps mixed gas from the junction 3 to the patient interface 4. The pump 8 is a variable speed pump such as a variable speed blower (e.g. a fan blower) that can be modulated by a controller to control the flow of air from the air inlet to the junction. The mixed gas line 7 also comprises a flow sensor, such as mixed gas flow sensor 17, which measures the flow of gas in mixed gas line 7. The mixed gas line 7 also comprises a pressure sensor, such as mixed gas pressure sensor 12, which measures the pressure of the mixed gas in the mixed gas line 7. The pressure sensor 12 is downstream of the pump 8. Optionally, the mixed gas flow sensor 17 is downstream of the pump 8. Optionally, the mixed gas line comprises an air filter such as bacteria filter 13 which filters mixed gas before reaching the patient interface 4.

The oxygen line 5 comprises an oxygen control valve 9, which is a proportional valve such as a proportional solenoid. The oxygen control valve 9 is positioned downstream of the oxygen inlet 1 and upstream of the junction 3 to modulate the flow of oxygen from the oxygen inlet 1 to the junction 3. The oxygen line 5 also comprises an oxygen flow sensor 10, e.g. downstream of the oxygen valve 9 which measures the flow of gas through the oxygen line 5. Optionally, the ventilator comprises a pressure regulator 14, e.g. if the oxygen inlet 1 is connected to an unregulated source of oxygen.

The air line 6 optionally comprises a check valve 18 downstream of the air inlet 2 and upstream of the junction 3. The check valve 18 can be used, e.g. to prevent escape of oxygen from the oxygen line 5.

Optionally, the ventilator comprises a valve, such as exhalation valve 15, which opens to exhaust gas from the ventilator during an exhalation phase and is closed during an inhalation phase. The exhalation valve 15 can be comprised by, e.g. the mixed gas line 7 downstream of the pump 8. Upstream of the exhalation valve 15, e.g. downstream of the pump 8, the mixed gas line 7 optionally comprises a check valve 16. Such a check valve can be used, e.g. to prevent exhalation gas from the patient from backflowing through and cross-contaminating pump 8. The exhalation valve 15 can optionally be a normally-open valve (e.g. solenoid) to allow free breathing by the patient in case of ventilator malfunction.

The ventilator further comprises a controller 24 which modulates the oxygen control valve 9 and the pump 8 to control parameters of the mixed gas such as oxygen content and pressure. The controller is configured to obtain feedback from the oxygen flow sensor 10, the mixed gas flow sensor 17, and the pressure sensor 12 to correct its modulation of the oxygen control valve 9 and the pump 8 and accurately achieve the parameters targets of the mixed gas. Optionally, the controller is configured to modulate an exhalation valve 15 such that the exhalation valve 15 is open during an exhalation phase and is closed during an inhalation phase.

Through insight of the inventor, such a ventilator having a pump downstream of the junction and, e.g. a controller as taught herein (e.g. any taught in Example 4 through Example 6), provides one or more of the following advantages. It can provide a simple control mechanism. For example, the pump can control both flow/volume and pressure delivered to the patients while the oxygen valve can function to maintain a set oxygen content and function as a secondary control flow/volume and pressure delivered. Additionally, oxygen mixing can be more uniform. Additionally, this embodiment may also yield more accurate flow/volume and pressure delivery as the pump can be used as the primary control mechanism for actual flow/volume and/or pressure delivery to the patient. Such an unexpected property provides an additional surprising advantage in the event mixing becomes off (e.g. if the oxygen valve is not perfectly in sync with a mixing algorithm) because the flow/volume and pressure delivery will be still accurate because the pump can ensures the accurate flow and/or pressure delivery.

Example 3 Ventilator with a Mixing Chamber

Figure 3:
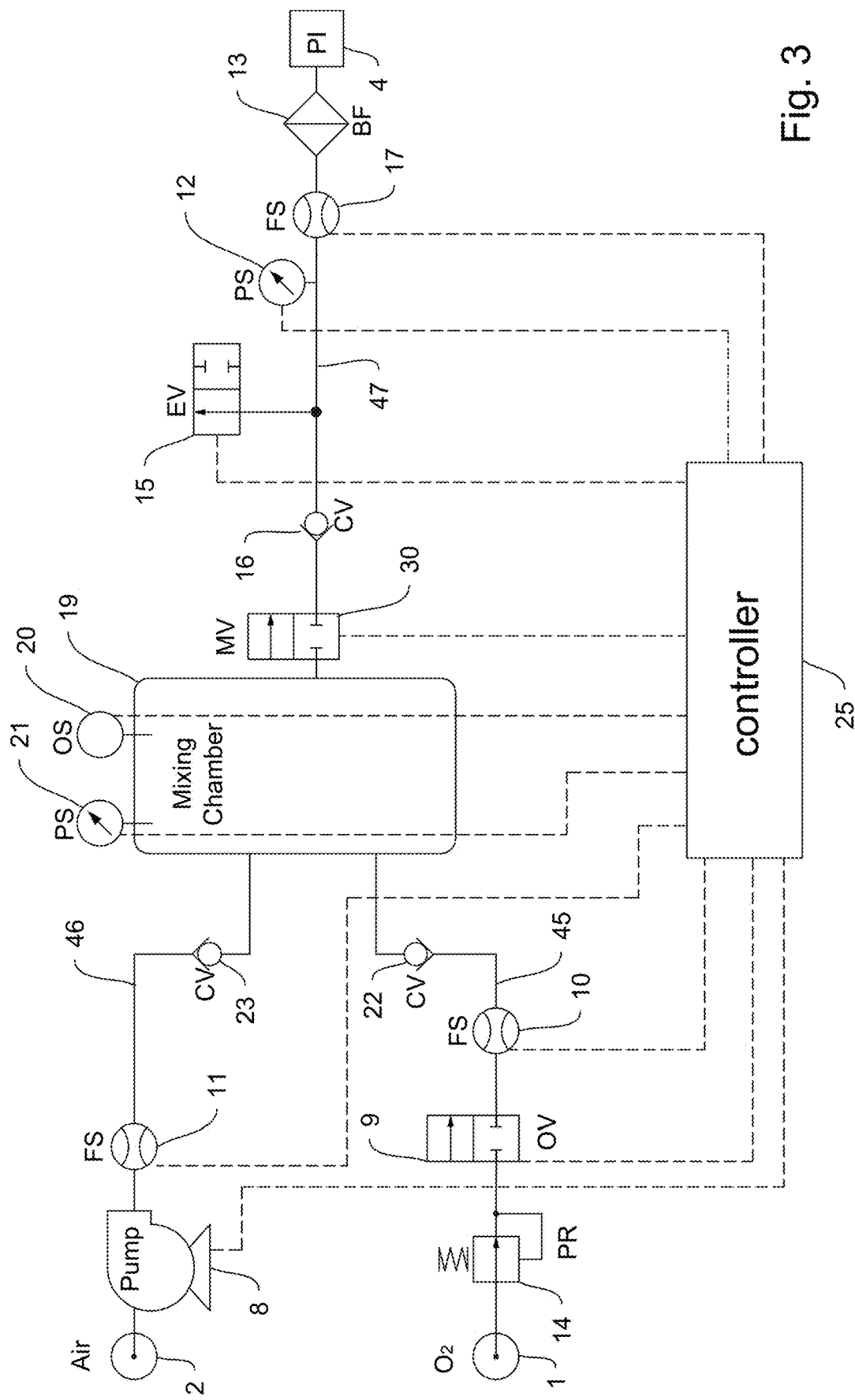
FIG. 3 depicts a ventilator of the invention.

One embodiment of the invention provides a ventilator having a junction comprising a mixing chamber downstream of an oxygen inlet and an air inlet and having a pump upstream of the mixing chamber. An example of such a ventilator is depicted in FIG. 3.

The ventilator comprises an oxygen inlet 1, an air inlet 2, an air/oxygen junction comprising a mixing chamber 19 downstream of the inlets 1,2 and a patient interface 4 downstream of the mixing chamber 19. Oxygen is conveyed through oxygen line 45, which is a gas conduit, from the oxygen inlet 1 to the mixing chamber 19. Air is conveyed through air line 46, which is a gas conduit, from the air inlet 2 to the mixing chamber 19. Air and oxygen are mixed in the mixing chamber to form a mixed gas which is conveyed from the mixing chamber 19 to the patient interface 4 by mixed gas line 47, which is a gas conduit. Alternatively, air and oxygen can be mixed upstream of the mixing chamber (not shown).

The oxygen line 45 comprises an oxygen control valve 9, which is a proportional valve such as a proportional solenoid. The oxygen control valve 9 is positioned downstream of the oxygen inlet 1 and upstream of the mixing chamber 19 to modulate the flow of oxygen from the oxygen inlet 1 to the mixing chamber. The oxygen line 45 also comprises an oxygen flow sensor 10, e.g. downstream of the oxygen control valve 9, which measures the flow of gas through the oxygen line 45. Optionally, the ventilator comprises a pressure regulator 14, e.g. if the oxygen inlet 1 is connected to an unregulated source of oxygen.

Figure 4:
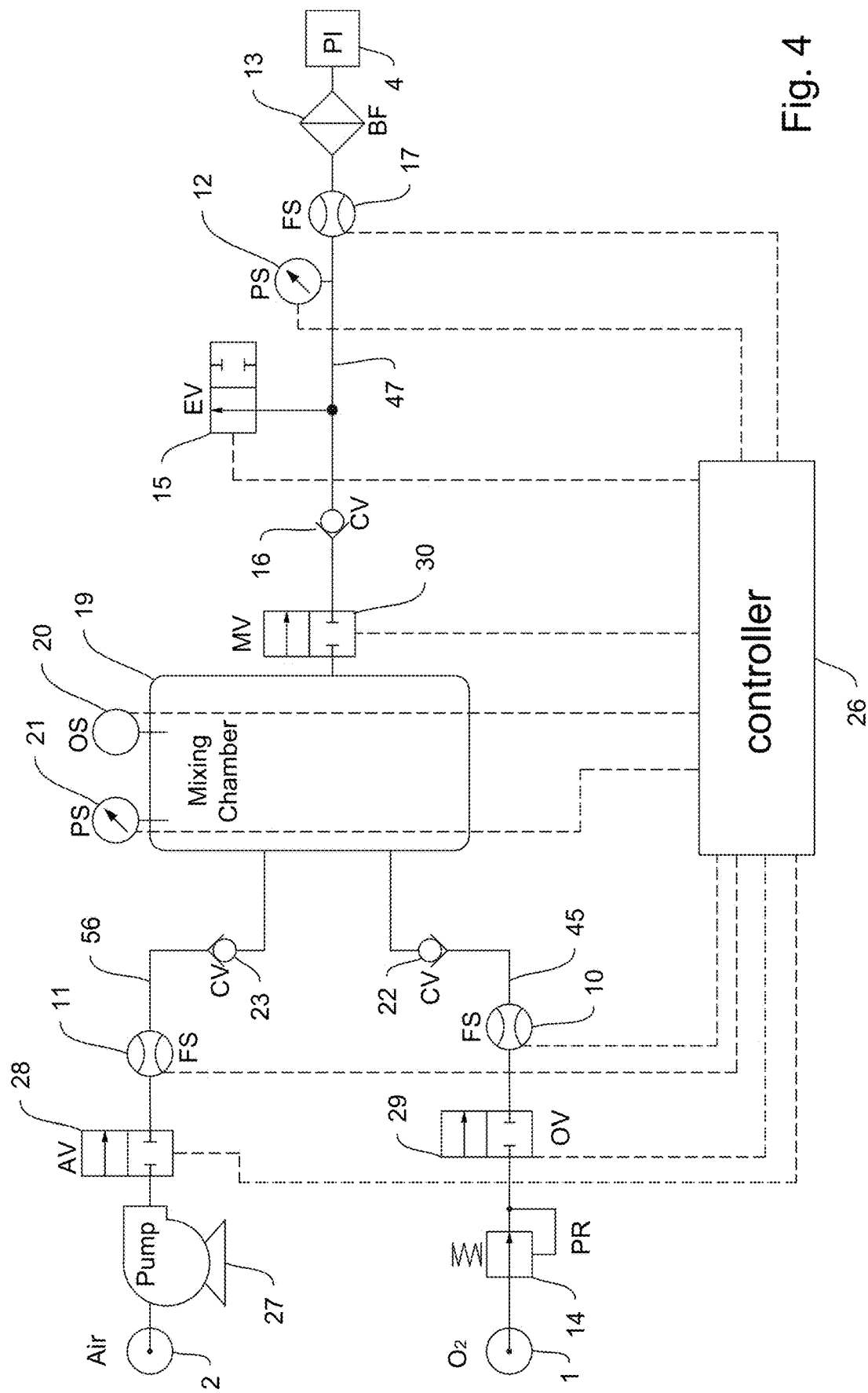
FIG. 4 depicts a ventilator of the invention.

The air line 46 comprises a pump 8 downstream of the air inlet 2 and upstream mixing chamber 19, which pumps mixed gas from the air inlet 2 to the mixing chamber 19. The pump 8 is optionally a variable speed pump such as a variable speed blower (e.g. a fan blower) that can be modulated by a controller to control the flow of air from the air inlet 2 to the mixing chamber 19. As an alternative to a variable speed pump, the ventilator can comprise air line 56 comprising, as an air flow modulator, a control valve 28 downstream of a constant speed pump 27 and upstream of the mixing chamber 19, as depicted in FIG. 4, wherein the control valve 28 is modulated by a controller 26 to control the air flow. The air line 46 also comprises a flow sensor, such as air flow sensor 11 which measures the flow of gas through the air line 46.

The mixed gas line 47 comprises a pressure sensor, such as mixed gas pressure sensor 12, which measures the pressure of the mixed gas in the mixed gas line 47. The mixed gas line 47 further comprises a control valve such as mixed gas control valve 30, which can be a proportional valve, that is controlled by the controller to modulate the flow of mixed gas from the mixing chamber 19 to the patient. Optionally, the mixed gas line comprises an air filter such as bacteria filter 13 which filters air before reaching the patient interface 4.

The mixing chamber 19 comprises a pressure sensor 21 which provides pressure feedback to the controller 25 and, optionally comprises an oxygen sensor 20, which measures the oxygen concentration in the mixing chamber and provides oxygen concentration feedback to the controller 25. The mixing chamber 19 is filled with gas from the oxygen line 45 and the air line 46 to provide a mixing chamber gas having an oxygen content equal to that of the target oxygen content of the mixed gas and having a pressure substantially greater than that of the mixed gas (e.g. about 10 mbar greater). Mixing chamber 19 provides a pressurized reservoir with no moving parts in its lumen and has a fixed physical volume such that gas is released, as needed, to the mixed gas line 47 by the mixed gas valve 30. Optionally, the physical volume and pressure of the mixing chamber is configured to provide at least a tidal volume, i.e. the volume of one breath, for the patient.

Optionally, the ventilator comprises a valve, such as exhalation valve 15, which opens to exhaust gas from the ventilator during an exhalation phase and is closed during an inhalation phase. The exhalation valve 15 is comprised by the mixed gas line 47 downstream of the mixing chamber 19 and upstream of the patient interface 4. Upstream of the exhalation valve 15 and downstream of the mixing chamber 19, the mixed gas line optionally comprises a check valve 16. Such a check valve can be used, e.g. to prevent exhalation gas from the patient from backflowing through and cross-contaminating the mixing chamber The exhalation valve 15 can optionally be a normally-open valve (e.g. solenoid) to allow free breathing by the patient in case of ventilator malfunction.

The ventilator further comprises a controller 25 or 26 which is configured to pressurize the mixing chamber 19 at a level substantially greater (e.g. about 10 mbar greater) than the mixed gas line 47. Specifically, controller 25 modulates the oxygen control valve 9 and the air flow modulator (e.g. pump 8 or valve 28) to control parameters of the mixing chamber gas such as oxygen content and mixing chamber pressure. The controller is configured to obtain feedback from the oxygen flow sensor 10, the air flow sensor 11, the pressure sensor 21, and optionally, the oxygen sensor 20, to correct its modulation of the oxygen control valve 9 and the pump 8 and accurately impart the desired parameters of the mixing chamber gas. The controller 25 is further configured to modulate the mixed gas control valve 30 to control the pressure, volume, and/or flow rate of mixed gas that flows from the mixing chamber 19 to the patient and optionally obtain feedback from a mixed gas pressure sensor 12 and/or mixed gas flow sensor 17 to correct its modulation of the mixed gas control valve 30 and accurately achieve the pressure target, flow target, or volume target. Optionally, the controller is configured to modulate an exhalation valve 15 such that the exhalation valve 15 is open during an exhalation phase and is closed during an inhalation phase.

Through insight of the inventor, a ventilator comprising a mixing chamber as taught herein, can deliver flow/volume and pressure to the patient with high accuracy with uniform oxygen mixing throughout the breath delivery.

Another optional advantage of a ventilator comprising a mixing chamber as taught herein, is that a modular ventilator configuration, e.g. with a disconnectable oxygen line, can be easily designed and implemented and optionally facilitates burden-free servicing.

Example 4 Ventilator Controller with Cascaded Feedback Control Loop Having an Outer Loop and Inner Loops One embodiment of the invention provides a ventilator having as feed lines an oxygen line and an air line that join to provide a gas mixture to a junction, wherein gas flow through each feed line to the junction can be controlled using a respective flow modulator e.g. as detailed in any of Example 1 through Example 3. In this embodiment, the parameters of the gas mixture at or downstream of the junction depend on the flow through each feed line that feeds the junction. Specifically, the pressure and flow rate of the gas are functions of the total (i.e. collective) flow through the feed lines and the oxygen content of gas mixture is a function of the ratio or relative flow through the feed lines.

The ventilator comprises a controller that controls the oxygen flow modulator and the air flow modulator to produce a gas mixture having a set of parameter targets. The oxygen flow modulator is, for example, a proportional valve comprised by the oxygen line. The air flow modulator is, for example, a variable speed pump comprised by the air line or downstream of the air/oxygen junction, or a proportional valve comprised by the air line.

The set of parameter targets comprises a target oxygen content of the gas mixture and one or more of a target pressure of the gas mixture, a target flow rate ('flow') of the gas mixture, and a target volume (e.g. target tidal volume) of the gas mixture. The controller provides setpoints based on the parameter targets. For example, the parameter target can be a constant target (e.g. a constant pressure) and the controller provides the target as a setpoint. As another example, the parameter target can be a target shape (e.g. pressure shape) having a plurality of discrete or relative parameter values and the controller provides a plurality of setpoints, for example, wherein the plurality of parameter values are time-dependent setpoints and the controller continuously updates a setpoint corresponding to the target value at the instant time.

The controller calculates a target flow of a gas that flows through one or more feed lines based on the parameter targets of the gas mixture such that the flow targets of the feedline gases impart the parameter targets of the gas mixture (e.g. oxygen content and at least one of pressure and flow). At least two of the oxygen feed line, the air feed line, and a line downstream of the junction (e.g. mixed gas feed line) comprise a respective flow sensor that sends feedback of the actual flow through the respective line to the controller. The controller can be configured to use a first equation that relates the flow through each line to each other. For example, the total flow downstream of the junction (i.e. gas mixture flow) is equal to the sum of the flows through the oxygen line and the air line. As another example, the flow through one of the feed lines is equal to the difference between the flow of the other feed line and the total flow downstream of the junction. The controller can also be configured to use a second equation that relates the oxygen content of the gas mixture to the respective oxygen content and respective flows of the oxygen line and the air line.

To impart a target pressure of the gas mixture, the controller is configured to calculate a flow target (e.g. mass flow) of the gas mixture using third equation that estimates the relationship of flow to pressure. The relationship of pressure and flow (or cumulative flow, i.e. volume delivered) is affected by certain variables. For example, in embodiments wherein the gas mixture is delivered to a mixing chamber, the container size of the mixing chamber affects the relationship of flow and pressure. In embodiments wherein the gas mixture is delivered directly to a patient, compliance of the patient system (e.g. lung and tube compliance) has a dramatic effect on the relationship of flow and pressure.

The target gas mixture flow is a command of the first feedback loop. The controller is configured to use a first feedback loop that corrects the target gas mixture flow using feedback received from a pressure sensor. Based on the calculated target gas mixture flow, the controller commands (i.e. calculates in this example) respective flow targets for the air line and the oxygen line using one or more equations that relate the gas mixture flow and oxygen content to respective flows and oxygen contents of the oxygen line and the air line, e.g. as detailed above.

The controller is configured to use a second feedback loop for control of the air flow modulator to impart the calculated air flow target. The controller is configured to use a third feedback loop for control of the oxygen flow modulator to impart the calculated oxygen flow. For each feedback loop, the controller corrects its command to the respective flow modulator after comparing the calculated target flow to actual flow. The actual flow is derived from feedback received from one or more flow sensors. For example, the actual flow value of the line can be obtained directly from a flow sensor comprised by the line, or it can be calculated using feedback from flow sensors of other lines, wherein flow of the gas mixture is the sum of the oxygen flow and the air flow.

Accordingly, this example demonstrates a cascaded feedback control loop that comprises the first feedback control loop as an outer loop and each of the second and third feedback loops as inner loops. Specifically, flow values are commanded by the first feedback loop to achieve a target gas mixture pressure, and the second and third feedback loops use the commanded target flow values as setpoints and achieve the setpoints by commanding respective flow modulators.

The cascaded feedback loop configuration taught in this example is useful in embodiments of the present invention, e.g. the ventilators detailed in any of Example 1, Example 2, or Example 3. For example, in embodiments that deliver gases from air and oxygen feed lines to a patient interface (e.g. without an intermediate mixing chamber that is pressurized to an overpressure), the controller can be used to control the delivery of gases to the patient interface. As another example, in embodiments that have a mixing chamber downstream of air and oxygen feed lines, the controller can be used to control the delivery of gases to the mixing chamber.

Through insight of the inventor, ventilators of the invention can use this feedback loop configuration to provide a superior ventilator having precise control of pressure and air/oxygen mixing.

Example 5 Ventilator Controller Feedback Control Loops

FIG. 5, FIG. 6A, FIG. 6B, and FIG. 7 depict examples of useful feedback loops which can be used by the controller to obtain a target pressure and a target oxygen content. Each of these feedback loops are useful in embodiments of the present invention, e.g. the ventilators detailed in any of Example 1, Example 2, or Example 3. For example, in embodiments that deliver gases from air and oxygen feed lines to a patient interface (e.g. without an intermediate mixing chamber that is pressurized to an overpressure), the feedback loops can be used to control the delivery of gases to the patient interface. As another example, in embodiments that have a mixing chamber downstream of air and oxygen feed lines, the feedback loops can be used to control the delivery of gases to the mixing chamber. In the figures, gas flow is depicted by solid lines and data flow and controller commands are depicted by dashed lines.

FIG. 5 depicts a pressure feedback loop that commands a flow target of a gas mixture to achieve a target pressure (e.g. in a patient interface or a mixing chamber), and splits the command into a target air flow and a target oxygen flow based on a target oxygen content. Target air flow is optionally controlled by a controller configured to a use an air flow feedback loop, as depicted in FIG. 6A. Target oxygen flow is optionally controlled by a controller configured to a use an oxygen flow feedback loop, as depicted in FIG. 6B.

The ventilator is optionally configured to use a cascaded feedback loop, wherein the cascaded feedback loop comprises a pressure loop as an outer loop that calculates flows that, when imparted by flow modulators, produce a gas mixture with a desired pressure setpoint, and wherein the cascaded feedback loop further comprises inner loops that command respective flow modulators that impart the calculated flows, e.g. as detailed in Example 4. Optionally, the ventilator comprises a controller configured to use a feedback loop that contains an outer loop and two parallel inner loops, each within the outer loop, e.g. as depicted in FIG. 7. In FIG. 7, the outer loop is a pressure feedback loop. A first inner loop is an air flow feedback loop that commands an air flow modulator. A second inner loop is an oxygen flow feedback loop that commands an oxygen flow modulator. For each feedback loop, the controller provides at least one setpoint based on a target for a gas parameter, provides a command configured (e.g. calibrated) to produce the setpoint, obtains the actual value of the gas parameter from a sensor as feedback from the command, compares the actual value to the setpoint to produce a command error (i.e., the difference between the setpoint and the actual value), and modifies a subsequent command based on the command error in real time. As the setpoint for a feedback loop can often be the target itself (e.g. as opposed to a setpoint calculated based on the target), the term "target" is sometimes used herein when referring to the setpoint of a feedback loop; however, it is to be understood that a setpoint can alternatively be a setpoint provided (e.g. calculated) based on the target rather than the target itself.

The pressure feedback loop (e.g. the pressure loop of FIG. 5 or FIG. 7) is configured to impart the target pressure (e.g. in a "patient system" as shown, or in any alternative system component such as a mixing chamber) by commanding (e.g. calculating) a target flow of the gas mixture. An algorithm is used to provide a target oxygen flow and a target air flow based on the mixed gas flow target and the target oxygen content. The air flow loop is configured to achieve the target air flow by commanding the air flow modulator. The oxygen flow loop is configured to achieve the target oxygen flow by commanding the oxygen flow modulator.

As depicted in the feedback loop of FIG. 5 and FIG. 7, the controller can be configured to perform the following steps:

A. A target pressure (e.g., a constant pressure value, or one of various pressure shapes such as adjustable rise time setting) is obtained. For example, if the target pressure is the target pressure of the mixed gas that's delivered to the patient, the target pressure can be set by user input (e.g. by a clinician). As another example, if the target pressure is the target pressure of an optional mixing chamber, the target pressure of the mixing chamber can be calculated based on a target pressure of the mixed gas, e.g. a defined overpressure of the maximum target pressure of the mixed gas. The controller can then provide a pressure setpoint based on the target pressure (e.g. wherein the setpoint is a point in a target pressure shape or wherein the setpoint is the constant pressure of a target pressure comprising constant pressure).

B. Summing junction of pressure target and pressure feedback. A comparison is made between the pressure target and the pressure feedback, i.e. actual pressure measured via a pressure sensor in the circuit.

C. A pressure error is calculated from the comparison of the pressure target and the pressure feedback. Specifically, the pressure error is the difference between the pressure target and the pressure feedback.

D. The pressure error becomes the input to the gas mixture flow target controller (e.g. mixed gas controller or mixing chamber gas controller) which corrects the pressure command, i.e. modifies the previous pressure command, based on the pressure error. The pressure command is a command configured to produce the target pressure. The gas mixture flow target controller (labeled "flow target controller") produces a gas mixture flow target as the pressure command, e.g. wherein the gas mixture flow target is the flow target value of a mixed gas comprising oxygen from the oxygen line and air from the air line which reaches the patient or, if a mixing chamber is provided, the gas mixture flow target is the target total flow of oxygen and air fed to a mixing chamber. The control cycle can be, e.g. 1-5 msec depending on the performance requirements. The feedback control mechanism can be, e.g. proportional, integral, derivative, PI, PID, feedforward, or a modified form thereof.

E. The pressure command (i.e. mixed gas mixture flow target) is input into the $FiO_2$ algorithm.

F. The $FiO_2$ (Fraction of Inspired Oxygen) algorithm calculates a target air flow and a target oxygen flow based on the gas mixture flow target and the target oxygen content. The target oxygen content is obtained, e.g. from user input of a $FiO_2$ setting. Specifically, the gas mixture flow target is split into a target air flow and a target oxygen flow based on the target oxygen content.

G. The air flow target is input to the air flow controller

H. The air flow controller commands the air flow modulator to achieve the target air flow. The air flow modulator is, for example, a variable speed pump (e.g. a dynamic pump) in the air line or mixed gas line or a proportional valve in the air line downstream of a pump (e.g. dynamic pump). The air flow controller can, for example, meter air flow from a flow sensor (e.g. measured directly in the air line or calculated as the difference between the flow of the gas mixture and the flow of oxygen) and obtain the actual air flow as feedback for comparison with the target air flow to produce an air flow error and correct the air flow command. The feedback control mechanism can be, e.g., proportional, integral, derivative, PI, PID, feedforward, or a modified form thereof.

I. The oxygen flow target is input to the oxygen flow controller

J. The oxygen flow controller commands the oxygen flow modulator to achieve the oxygen flow target. The oxygen flow modulator is, for example, a proportional valve in the oxygen line. The oxygen flow controller meters, for example, oxygen flow from a flow sensor in the oxygen line and obtains the actual oxygen flow as feedback for comparison with the target oxygen flow to produce an oxygen flow error and correct the oxygen flow command. The feedback control mechanism can be, e.g., proportional, integral, derivative, PI, PID, feedforward, or a modified form thereof.

K. Air flow output—Air flows from the air flow modulator downstream to the junction.

L. Oxygen flow output—Oxygen flows from the oxygen flow modulator downstream to the junction.

M. Summing junction of air flow and oxygen flow outputs. The oxygen flow output merges with the air flow output to form a gas mixture.

N. Gas mixture. The gas mixture output, i.e., a mixture comprising the air flow output plus oxygen flow output, is provided. The gas mixture can be, e.g. mixed gas for delivery to the patient or can be a gas mixture delivered to a mixing chamber. The pressure of the gas mixture is function of at least the flow of the gas mixture, specifically the volume delivered which is an integration of flow, noting that the relationship of pressure v.s. flow or volume delivered can depend on physical volume or compliance of the target space to which the gas mixture is delivered (e.g. patient system or mixing chamber). For example, in an embodiment wherein the gas mixture is fed to a mixing chamber or directly to a patient, the pressure of the gas mixture can depend, at least in part, on the volume of the mixing chamber or the patient system, respectively. When the gas mixture is the mixed gas delivered to the patient (e.g. rather than to an intermediate mixing chamber), the pressure is affected by compliance of the patient system (e.g. static and/or dynamic compliance) such as patient-lung compliance and tubing compliance. The patient system can comprise the patient and the patient interface and includes, for example, a patient circuit, inline humidifier, inline bacteria filter, mask and any optional component inline with the patient tubing. These features can introduce additional compliance which can be corrected by feedback control of the pressure.

O. The pressure sensor measures the actual pressure of the gas mixture and provides feedback to the gas mixture controller. Optionally, the gas mixture is the mixed gas provided to the patient and the pressure sensor is located, e.g., either in the patient circuit or upstream in the ventilator. Alternatively, the gas mixture is optionally the mixing chamber gas and the pressure sensor is comprised by the mixing chamber.

P. Pressure feedback—The actual pressure of the gas mixture measured by the pressure sensor is obtained by the controller for comparison with the target pressure in the summing junction, as detailed in step B, and the feedback loop is continuously repeated in real time.

FIG. 6A depicts a feedback control loop that can optionally be used by an air flow controller, e.g. the air flow controller of step H in the feedback loop detailed in the example above. As depicted in FIG. 6A, the feedback control loop comprises the following steps:

G. The air flow target is provided.

H1. Summing junction of air flow target and air flow feedback. A comparison is made between the air flow target and the air flow feedback, e.g. the actual air flow measured in the air line or calculated based on the difference between measured oxygen flow and measured gas mixture flow.

H2. An air flow error is calculated from the comparison of the air flow target and the air flow feedback. Specifically, the air flow error is the difference between the air flow target and the air flow feedback.

H3. The air flow error becomes the input to the air flow controller which corrects the air flow command, i.e. modifies the previous air flow command, based on the air flow error. The feedback control mechanism can be, e.g. proportional, integral, derivative, PI, PID, feedforward, or a modified form thereof.

H4. The air flow command is provided to the air flow modulator. The air flow command is, for example, a signal such as a voltage provided to the air flow modulator.

H5. The air flow modulator receives the air flow command and assumes a position (e.g. pump speed or valve position), e.g. that is dependent on the signal level of the command. The air flow modulator is, for example, a variable speed pump (e.g. variable speed dynamic pump) in the air line or downstream of the air/oxygen junction or a proportional valve in the air line downstream of a pump (e.g. fixed speed dynamic pump).

K. Air flow output—Air flows downstream from the air flow modulator

H6. The air flow sensor, provided in the air line, measures the actual air flow. As an alternative to using an air flow sensor, an air flow calculator can be used to calculate the air flow feedback, e.g. as the difference between measured oxygen flow and measured gas mixture flow.

H7. The actual air flow (e.g. measured by the air flow sensor) is provided to the controller as air flow feedback for comparison with the target air flow in the summing junction, as detailed in step H1, and the feedback loop is continuously repeated in real time.

FIG. 6B depicts a feedback control loop that can optionally be used by an oxygen flow controller, e.g. the oxygen flow controller of step J in the feedback loop detailed in the example above.

G. The oxygen flow target is provided

J1. Summing junction of oxygen flow target and oxygen flow feedback. A comparison is made between the oxygen flow target and the oxygen flow feedback, i.e. the actual oxygen flow measured in the oxygen line or calculated based on the difference between measured air flow and measured gas mixture flow.

J2. An oxygen flow error is calculated from the comparison of the oxygen flow target and the oxygen flow feedback. Specifically, the oxygen flow error is the difference between the oxygen flow target and the oxygen flow feedback.

J3. The oxygen flow error becomes the input to the oxygen flow controller which corrects the oxygen flow command, i.e. modifies the previous oxygen flow command, based on the oxygen flow error. The feedback control mechanism can be, e.g. proportional, integral, derivative, PI, PID, feedforward, or a modified form thereof.

J4. The oxygen flow command is provided to the oxygen flow modulator. The oxygen flow command is, for example, a signal such as a voltage provided to the oxygen flow modulator.

J5. The oxygen flow modulator receives the oxygen flow command and assumes a position (e.g. valve position), e.g. that is dependent on the signal level of the command. The oxygen flow modulator is, for example, a proportional valve in the oxygen line downstream of the oxygen inlet.

L. Oxygen flow output—Oxygen flows downstream from the oxygen flow modulator

J6. The oxygen flow sensor, provided in the oxygen line, measures the actual oxygen flow. As an alternative to using an oxygen flow sensor, an oxygen flow calculator can be used to calculate the oxygen flow feedback, e.g. as the difference between measured air flow and measured gas mixture flow.

J7. The actual oxygen flow (e.g. measured by the oxygen flow sensor) is provided to the controller as oxygen flow feedback for comparison with the target oxygen flow in the summing junction, as detailed in step J1, and the feedback loop is continuously repeated in real time.

Through insight of the inventor, ventilators of the invention can use the feedback loops of this example to provide a superior ventilator having precise control of pressure and air/oxygen mixing.

Example 6 Ventilator Controller Feedback Control Loops

This example details a controller configured to use one or more feedback loops for delivering mixed gas to a patient with other forms of targeting such as volume targeting or flow targeting.

FIG. 9, FIG. 6A, FIG. 6B, and FIG. 10 depict examples of useful feedback loops which can be used by the controller to obtain a target volume or flow and a target oxygen content. Each of these feedback loops are useful in embodiments of the present invention, e.g. the ventilators detailed in in Example 1 or Example 2

Figure 9:
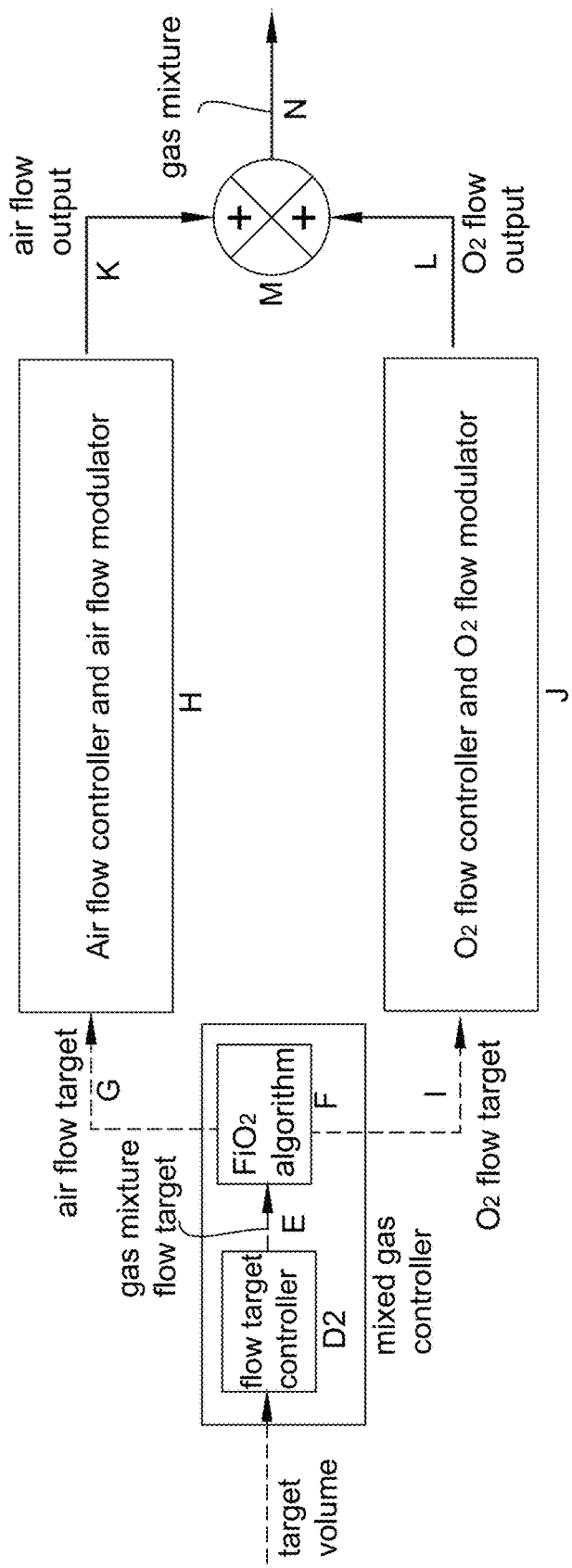
FIG. 9 depicts a feedback control loop used by a controller useful in the present invention.

FIG. 9 depicts a volume or flow controller that commands a flow target of a gas mixture to achieve a target flow in a patient interface and splits the command into a target air flow and a target oxygen flow based on a target oxygen content. The flow target is, for example, calculated based on a volume target (e.g. determined by a user inputted waveform such as sine wave or descending ramp or by a real time volume measurement and calculation of real time volume error). Target air flow is optionally controlled by a controller configured to a use an air flow feedback loop, as depicted in FIG. 6A. Target oxygen flow is optionally controlled by a controller configured to a use an oxygen flow feedback loop, as depicted in FIG. 6B.

Figure 10:
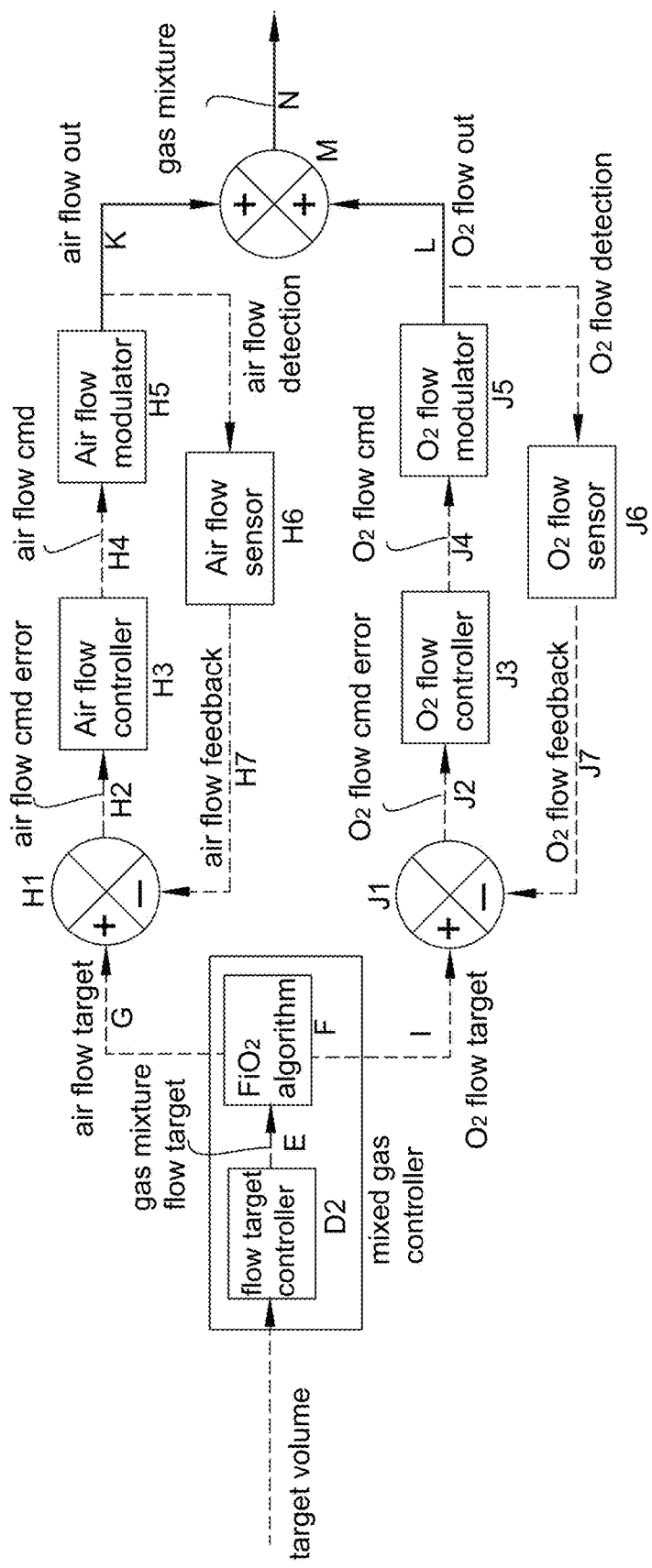
FIG. 10 depicts a feedback control loop used by a controller useful in the present invention.

Optionally, the ventilator comprises a controller configured to use parallel inner loops, each having a setpoint (labeled "air flow target" and "O$_2$ flow target", respectively) determined by a controller such as a controller which utilizes an a FiO$_2$ algorithm, e.g. as depicted in FIG. 10. A first loop is an air flow feedback loop that commands an air flow modulator. A second loop is an oxygen flow feedback loop that commands an oxygen flow modulator. The mixed gas controller provides the air flow target and oxygen flow target which are used as setpoints (i.e. targets) by the air flow controller and oxygen flow controller, respectively. For each feedback loop, the controller provides a flow, provides a command configured (e.g. calibrated) to achieve the target flow, obtains or calculates the actual value of the flow from a sensor as feedback from the command, compares the actual flow value to the target flow to produce a command error (i.e., the difference between the target and the actual value), and modifies a subsequent command based on the command error in real time.

An algorithm is used to provide a target oxygen flow and a target air flow based on the mixed gas flow target and the target oxygen content. The air flow loop is configured to achieve the target air flow by commanding the air flow modulator. The oxygen flow loop is configured to achieve the target oxygen flow by commanding the oxygen flow modulator.

As depicted in the control diagrams of FIG. 9 and FIG. 10, the controller can be configured to perform the following steps:

An input (e.g. user input) such as target volume, as shown, or flow target, is obtained by the mixed gas controller.

D2. If a volume target was provided as the input, a mixed gas flow target is provided based on the input. For example, the mixed gas controller can comprise a functional component (labeled "flow target controller") that determines (e.g. calculates) a flow target based on the volume target shape or real time measured volume error.

E. the mixed gas flow target is input into the FiO$_2$ algorithm.

F. The FiO$_2$ (Fraction of Inspired Oxygen) algorithm calculates a target air flow and a target oxygen flow based on the gas mixture flow target and the target oxygen content. The target oxygen content is obtained, e.g. from user input of a FiO$_2$ setting. Specifically, the gas mixture flow target is split into an air flow target and an oxygen flow target based on the target oxygen content.

G. The air flow target is input to the air flow controller

H. The air flow controller commands the air flow modulator to achieve the target air flow. The air flow modulator is, for example, a variable speed pump (e.g. a dynamic pump) in the air line or a mixed gas line or a proportional valve in the air line downstream of a pump (e.g. dynamic pump). The air flow controller can, for example, meter air flow from a flow sensor (e.g. measured directly in the air line or calculated as the difference between the flow of the gas mixture and the flow of oxygen) and obtain the actual air flow as feedback for comparison with the target air flow to produce an air flow error and correct the air flow command. The feedback control mechanism can be, e.g., proportional, integral, derivative, PI, PID, feedforward, or a modified form thereof.

I. The oxygen flow target is input to the oxygen flow controller

J. The oxygen flow controller commands the oxygen flow modulator to achieve the oxygen flow target. The oxygen flow modulator is, for example, a proportional valve in the oxygen line. The oxygen flow controller meters, for example, oxygen flow from a flow sensor in the oxygen line and obtains the actual oxygen flow as feedback for comparison with the target oxygen flow to produce an oxygen flow error and correct the oxygen flow command. The feedback control mechanism can be, e.g., proportional, integral, derivative, PI, PID, feedforward, or a modified form thereof.

K. Air flow output—Air flows from the air flow modulator downstream to the junction.

L. Oxygen flow output—Oxygen flows from the oxygen flow modulator downstream to the junction.

M. Summing junction of air flow and oxygen flow outputs. The oxygen flow output merges with the air flow output to form the mixed gas.

N. Gas mixture. The gas mixture output, i.e., the mixed gas comprising the air flow output plus oxygen flow output, is provided to the mixed gas line.

As depicted in FIG. 10, the air flow controller and the oxygen flow controller can be configured to use feedback loops to control respective modulators, e.g. as depicted in FIG. 6A and FIG. 6B, respectively.

FIG. 6A depicts a feedback control loop that can optionally be used by the air flow controller, e.g. the air flow controller of step H in the feedback loop detailed in the example above. As depicted in FIG. 6A, the feedback control loop comprises the following steps:

G. The air flow target is provided.

H1. Summing junction of air flow target and air flow feedback. A comparison is made between the air flow target and the air flow feedback, e.g. the actual air flow measured in the air line or calculated based on the difference between measured oxygen flow and measured gas mixture flow.

H2. An air flow error is calculated from the comparison of the air flow target and the air flow feedback. Specifically, the air flow error is the difference between the air flow target and the air flow feedback.

H3. The air flow error becomes the input to the air flow controller which corrects the air flow command, i.e. modifies the previous air flow command, based on the air flow error. The feedback control mechanism can be, e.g. proportional, integral, derivative, PI, PID, feedforward, or a modified form thereof.

H4. The air flow command is provided to the air flow modulator. The air flow command is, for example, a signal such as a voltage provided to the air flow modulator.

H5. The air flow modulator receives the air flow command and assumes a position (e.g. pump speed or valve position), e.g. that is dependent on the signal level of the command. The air flow modulator is, for example, a variable speed pump (e.g. variable speed dynamic pump) in the air line or downstream of the air/oxygen junction or a proportional valve in the air line downstream of a pump (e.g. fixed speed dynamic pump).

K. Air flow output—Air flows downstream from the air flow modulator

H6. The air flow sensor, provided in the air line, measures the actual air flow. As an alternative to using an air flow sensor, an air flow calculator can be used to calculate the air flow feedback, e.g. as the difference between measured oxygen flow and measured gas mixture flow.

H7. The actual air flow (e.g. measured by the air flow sensor) is provided to the controller as air flow feedback for comparison with the target air flow in the summing junction, as detailed in step H1, and the feedback loop is continuously repeated in real time.

FIG. 6B depicts a feedback control loop that can optionally be used by the oxygen flow controller, e.g. the oxygen flow controller of step J in the feedback loop detailed in the example above.

G. The oxygen flow target is provided

J1. Summing junction of oxygen flow target and oxygen flow feedback. A comparison is made between the oxygen flow target and the oxygen flow feedback, i.e. the actual oxygen flow measured in the oxygen line or calculated based on the difference between measured air flow and measured gas mixture flow.

J2. An oxygen flow error is calculated from the comparison of the oxygen flow target and the oxygen flow feedback. Specifically, the oxygen flow error is the difference between the oxygen flow target and the oxygen flow feedback.

J3. The oxygen flow error becomes the input to the oxygen flow controller which corrects the oxygen flow command, i.e. modifies the previous oxygen flow command, based on the oxygen flow error. The feedback control mechanism can be, e.g. proportional, integral, derivative, PI, PID, feedforward, or a modified form thereof.

J4. The oxygen flow command is provided to the oxygen flow modulator. The oxygen flow command is, for example, a signal such as a voltage provided to the oxygen flow modulator.

J5. The oxygen flow modulator receives the oxygen flow command and assumes a position (e.g. valve position), e.g. that is dependent on the signal level of the command. The oxygen flow modulator is, for example, a proportional valve in the oxygen line downstream of the oxygen inlet.

L. Oxygen flow output—Oxygen flows downstream from the oxygen flow modulator

J6. The oxygen flow sensor, provided in the oxygen line, measures the actual oxygen flow. As an alternative to using an oxygen flow sensor, an oxygen flow calculator can be used to calculate the oxygen flow feedback, e.g. as the difference between measured air flow and measured gas mixture flow.

J7. The actual oxygen flow (e.g. measured by the oxygen flow sensor) is provided to the controller as oxygen flow feedback for comparison with the target oxygen flow in the summing junction, as detailed in step J1, and the feedback loop is continuously repeated in real time.

Accordingly, this example details how volume or flow targeting can be used to deliver a mixed gas to a patient with feedback control of oxygen and flow modulators. Such volume- or flow-targets can be, e.g. provided as an alternative to pressure targeting for choosing by a user of the ventilator.

Example 7 Controller for a Ventilator with a Mixing Chamber

One embodiment of the invention provides a ventilator having an oxygen feed line, an air feed line, an oxygen flow modulator, and an air flow modulator, wherein the flow modulators modulate the flow of the respective gases to a junction comprising a mixing chamber, e.g. as detailed in Example 3. In this embodiment, the parameters of the mixing chamber gas depend on the flow through each line that feeds the mixing chamber. Specifically, the oxygen content of the gas mixture is a function of the ratio or relative flow through the feed lines, and given a fixed physical volume of the mixing chamber, the pressure in the mixing chamber is a function of the cumulative flow through the feed lines. The ventilator comprises a controller that controls the oxygen flow modulator and the air flow modulator to produce a mixing chamber gas having a set of parameter targets comprising a target oxygen content and target mixing chamber pressure. To pressurize the mixing chamber to a target mixing chamber pressure and target oxygen content, the controller can use one or more feedback loops, e.g. as detailed in Example 4 or in Example 5 and shown in FIG. 5, FIG. 6A, FIG. 6B, or FIG. 7.

The ventilator further comprises a mixed gas line that transmits gas from the mixing chamber to the patient and a mixed gas control valve in the mixed gas line that modulates flow of gas released from the mixing chamber to patient, e.g. as detailed in Example 3. In addition to the aforementioned feedback loops to control delivery of gas to the mixing chamber, the controller can be configured to use another feedback control loop for error correction of the mixed gas control valve to control delivery of mixed gas to the patient. An example of such a feedback control loop is depicted in FIG. 8. Accordingly, in this embodiment, the controller is optionally configured to use a first feedback loop (e.g. FIG. 5 or FIG. 7) to control the delivery of gas to the mixing chamber and a second feedback loop to control the delivery of gas from the mixing chamber to the patient (e.g. FIG. 8 or FIG. 11).

As depicted in the feedback loop of FIG. 8, the controller can be configured to perform the following steps to control delivery of gas from the mixing chamber to the patient:

Q. A target mixed gas pressure (e.g., a constant pressure value, or one of various pressure shapes such as adjustable rise time setting) is obtained, e.g. set by user input (e.g. by a clinician).

R. Summing junction of pressure target and pressure feedback. A comparison is made between the pressure target and the pressure feedback, i.e. actual pressure measured via a pressure sensor downstream of the mixed gas control valve.

S. A pressure error is calculated from the comparison of the pressure target and the pressure feedback. Specifically, the pressure error is the difference between the pressure target and the actual pressure.

T. The pressure error becomes the input to the mixed gas flow controller which corrects the mixed gas control valve command, i.e. modifies the previous mixed gas valve command, based on the pressure error. The feedback control mechanism can be, e.g. proportional, integral, derivative, PI, PID, feedforward, or a modified form thereof.

U. The mixed gas valve command is provided to the mixed gas control valve. The mixed gas valve command is, for example, a signal such as a voltage provided to the mixed gas control valve V. The mixed gas control valve receives the mixed gas valve command and assumes a position (e.g. valve position), e.g. that is dependent on the signal level of the command. The mixed gas control valve is, for example, a proportional valve the downstream of the mixing chamber.

W. The mixed gas is output, i.e., gas flows from the mixing chamber downstream towards the patient. The actual pressure of the mixed gas is function of the flow of the gas mixture, specifically the volume delivered which is an integration of flow. However, the actual pressure is also affected by other factors such as compliance of the patient system (e.g. static and/or dynamic compliance) such as patient-lung compliance and tubing compliance. The patient system comprises the patient and the patient interface and includes, for example, a patient circuit, inline humidifier, inline bacteria filter, mask and any optional component inline with the patient tubing. These features can introduce disturbances which can be corrected by feedback control of the pressure.

X. The pressure sensor measures the actual pressure of the mixed gas and provides feedback to the controller. The pressure sensor can be located, e.g., either in the patient circuit or upstream in the ventilator.

Y. Pressure feedback—The actual pressure of the mixed gas measured by the pressure sensor is obtained by the controller for comparison with the target pressure in the summing junction, as detailed in step R, and the feedback loop is continuously repeated in real time.

Figure 11:
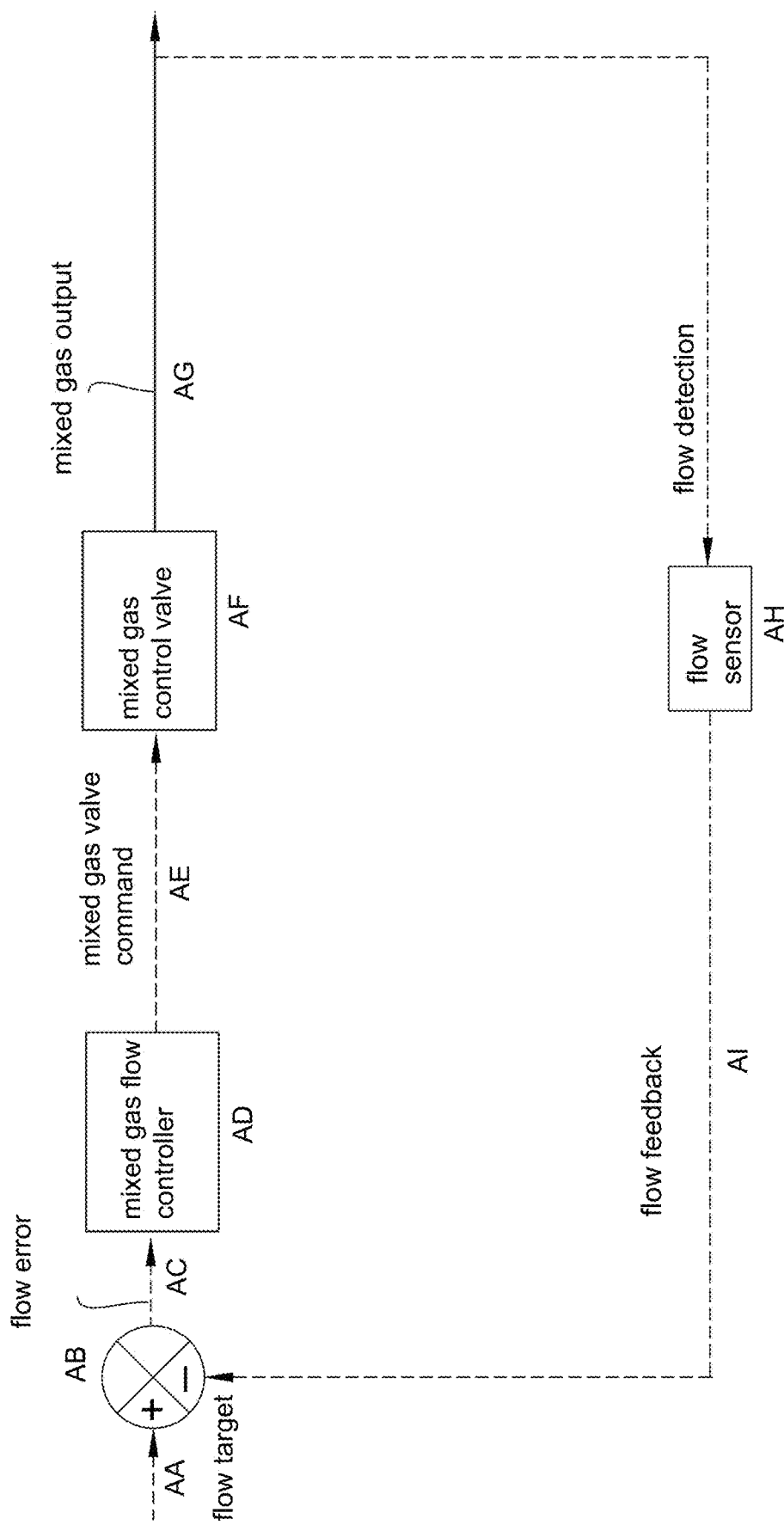
FIG. 11 depicts a feedback control loop used by a controller useful in the present invention.

As an alternative to the feedback loop depicted in FIG. 8, which modulates a mixed gas control valve to impart a target pressure in the mixed gas line, the controller can be configured to use a feedback loop which modulates the mixed gas control valve to impart a target flow or target volume (e.g. a target volume shape defined by one or more target flows). In this embodiment, the pressure target, pressure error, pressure detection, pressures sensor, and pressure feedback steps detailed above and shown in FIG. 8 can be substituted with a flow target, flow error, flow detection, flows sensor, and flow feedback, respectively. Additionally or alternatively, the flow target can be determined, e.g., calculated based on a volume target, (e.g. by a flow target controller as with flow target controller D2 of FIG. 9 which determines gas mixture flow target E). Specifically, as depicted in FIG. 11, the controller can be configured to perform the following steps to control delivery of gas from the mixing chamber to the patient:

AA. A mixed gas flow target is provided, e.g. by input by a user or determined based on a target volume shape or real time target volume error.

AB. Summing junction of flow target and flow feedback. A comparison is made between the flow target and the flow feedback, i.e. actual flow measured via a flow sensor in the mixed gas line.

AC. A flow error is calculated from the comparison of the flow target and the flow feedback. Specifically, the flow error is the difference between the flow target and the actual flow.

AD. The flow error becomes the input to the mixed gas flow controller which corrects the mixed gas control valve command, i.e. modifies the previous mixed gas valve command, based on the flow error. The feedback control mechanism can be, e.g. proportional, integral, derivative, PI, PID, feedforward, or a modified form thereof.

AE. The mixed gas valve command is provided to the mixed gas control valve. The mixed gas valve command is, for example, a signal such as a voltage provided to the mixed gas control valve AF. The mixed gas control valve receives the mixed gas valve command and assumes a position (e.g. valve position), e.g. that is dependent on the signal level of the command. The mixed gas control valve is, for example, a proportional valve in the downstream of the mixing chamber.

AG. The mixed gas is output, i.e., gas flows from the mixing chamber downstream towards the patient.

AH. The flow sensor measures the actual flow of the mixed gas and provides feedback to the controller.

AI. Flow feedback—The actual flow of the mixed gas measured by the flow sensor is obtained by the controller for comparison with the target flow in the summing junction, as detailed in step AB, and the feedback loop is continuously repeated in real time.

As detailed in this example, a ventilator comprising a mixing chamber can use one or more feedback loops for pressurizing the mixing chamber as well as one or more feedback loops for delivering mixed gas to a patient. Also as detailed in this example, the ventilator can be configured for delivering mixed gas to a patient with pressure targeting, volume targeting, flow targeting, or a combination thereof.
F Example 8 Calculation of Target Air Flow and Target Oxygen Flow According to the present invention, a controller can optionally be configured to use an FiO$_2$ algorithm, e.g. as in step F described in Example 5, to calculate a target air flow and a target oxygen flow based on the gas mixture flow target and the target oxygen content. The following example illustrates equations that can optionally be used to perform such a calculation.

In the equations that follow, the following variable definitions are used:
$F_A$=Target flow of air through the air line
$F_O$=Target flow of oxygen through the oxygen line
$F_M$=Target flow of a gas mixture (e.g. mixed gas or mixing chamber gas)
$O_A$=Oxygen content of air
$O_O$=Oxygen content of oxygen
$O_M$=Target oxygen content of mixed gas
$F_M$=Target flow of the mixed gas The following equation relates the oxygen content and flow rates of the three gasses (gas mixture M, air A, and oxygen O):

$$(O_M)(F_M)=(O_A)(F_A)+(O_O)(F_O) \quad \text{Equation 1:}$$

The following equation relates the flow rates of the three gasses:

$$F_M=F_A+F_O \quad \text{Equation 2:}$$

Substituting the identity of $F_M$ (from Equation 2) into Equation 1, provides:

$$(O_M)(F_A+F_O)=(O_A)(F_A)+(O_O)(F_O) \quad \text{Equation 3:}$$

As exemplary oxygen contents, consider the oxygen content of air $O_A$ is 0.21, the oxygen content of oxygen is 1, and an exemplary target oxygen content of the gas mixture is $O_M$ 0.26. Under these conditions, Equation 3 can be solved as:

$$F_A/F_O=14.8$$

Under these exemplary conditions, the ratio of air flow rate to flow rate is, for example, 14.8 to provide a target mixed gas oxygen content of 26%.

This example demonstrates the use of Equations 3 to determine the relative flows of oxygen and air.

Given a target gas mixture flow rate $F_M$ (e.g. determined based on a target pressure), Equation 2 can be used to determine the actual flow rates of the oxygen and air. Accordingly, this example also demonstrate the use of Equation 2 in combination with Equation 3 to determine the target flows of air and oxygen based on a target mixed gas flow.

The citations provided herein are hereby incorporated by reference for the cited subject matter.

What is claimed is:

1. A ventilator system comprising:
an air inlet connected to a first gas line;
an oxygen inlet connected to a second gas line;
a mixing chamber connected to both the first gas line and the second gas line;
an air pump and an air flow sensor both connected to the first gas line downstream of the air inlet and upstream of the mixing chamber;
an oxygen control valve and an oxygen flow sensor both connected to the second gas line upstream of the mixing chamber and downstream of the oxygen inlet;
a mixed gas pressure sensor and a mixed gas flow sensor both connected to a third gas line downstream of the mixing chamber and upstream of a patient interface;
a mixing chamber pressure sensor connected to the mixing chamber;
a controller operably connected to the air pump and the oxygen control valve, and further configured to receive measurement signals from the air flow sensor, the oxygen flow sensor, the mixed gas flow sensor, the mixed gas pressure sensor and the mixing chamber pressure sensor, and to implement a cascaded feedback loop that commands a flow target of a mixture of oxygen to air to achieve a target pressure, wherein the cascaded feedback loop comprises an outer pressure feedback loop and dual inner feedback loops, comprising an oxygen flow control feedback loop and an air flow control feedback loop, wherein the outer pressure feedback loop comprises the controller; and wherein the controlled is further configured to:
obtain a target pressure,
obtain a target oxygen content,
obtain a pressure reading from the mixed gas pressure sensor (the pressure feedback),
compare the pressure feedback to the target pressure,
determine a pressure error based on the comparison of the pressure feedback and the target pressure,
based on the pressure error, correct the mixed gas flow command
determine a target air flow command and a target oxygen flow command based on the pressure error,
control the air pump based on the target air flow command, and
control oxygen control valve based on the target oxygen flow command;
and wherein the oxygen flow control feedback loop comprises the controller:
obtain a target oxygen flow,
determine an oxygen flow command based on the target oxygen flow,
command the oxygen control valve with the oxygen flow command
determine actual oxygen flow in the second line by obtaining an oxygen flow reading from the oxygen flow,
compare the actual oxygen flow to the target oxygen flow,
determine an oxygen flow error based on the comparison of the actual oxygen flow feedback and the target oxygen flow,
based on the oxygen flow error, and
correct the oxygen flow command based on the oxygen flow error; and
and wherein the air flow control feedback loop comprises the controller:
obtain a target air flow,
provide an air flow command based on the target air flow,
command the air pump with the air flow command;
determine actual air flow in the first gas line by obtaining an air flow reading from the air flow sensor;

compare the actual air flow feedback to the target air flow;
determine an air flow error based on the comparison of the actual air flow and the target air flow, and
correct the air flow command based on the air flow error.

2. The ventilator system of claim 1, wherein an exhalation valve is connected to the third gas line downstream of the mixing chamber and upstream of the patient interface.

3. The ventilator system of claim 2, wherein the controller is configured to modulate a control signal for the exhalation valve based on a measurement signal received from the mixed gas pressure sensor.

4. The ventilator system of claim 3, wherein the controller is configured to identify an inhalation phase and an exhalation phase based on the measurement signal, and the controller is configured to modulate a control signal for the exhalation valve so that it closes the exhalation valve during an inhalation phase, and opens the exhalation valve during an exhalation phase.

5. The ventilator system of claim 1, wherein the target pressure is manually set by a user.

6. The ventilator system of claim 1, wherein the pressure error is used to modulate a control signal of at least one of the pump and the oxygen control valve.

7. The ventilator system of claim 1 further comprising:
a bacteria filter positioned in the third gas line downstream of the mixing chamber and upstream of the patient interface.

8. The ventilator system of claim 1 further comprising:
a pressure regulator connected to the second gas line between the oxygen inlet and the junction.

9. The ventilator system of claim 1 further comprising:
a high pressure oxygen source connected to the oxygen inlet.

10. The ventilator system of claim 1 further comprising:
a low pressure air source connected to the air inlet.

11. The ventilator system of claim 1, wherein the pump is a low pressure variable speed blower.

12. The ventilator system of claim 1, wherein the pump is configured to pressurize downstream gas to a pressure of no more than 140 millibar (mbar).

13. The ventilator system of claim 1, wherein the pump is configured to pressurize downstream gas to a pressure of no more than 70 millibar (mbar).

14. The ventilator system of claim 1 further comprising:
a mixed gas control valve connected to the third gas line downstream of the mixing chamber and upstream of the patient interface.

15. The ventilator system of claim 14, wherein the controller is configured to modulate a control signal for the mixed gas control valve based on measurement signals received from at least one of the mixing chamber pressure sensor and the mixed gas pressure sensor.

16. The ventilator system of claim 1 further comprising:
an oxygen sensor connected to the mixing chamber, wherein the controller is configured to receive oxygen concentration measurement signals from the oxygen sensor.

17. The ventilator system of claim 16, wherein the controller is configured to modulate a control signal for the oxygen control valve based on the received oxygen concentration measurement signals.

18. The ventilator system of claim 16, wherein the controller is configured to modulate a control signal for the pump based on the received oxygen concentration measurement signals.

19. The ventilator system of claim 1 further comprising:
an air flow control valve connected to the first gas line upstream of the air flow sensor and downstream of the air pump, wherein the air flow control valve is operably connected to the controller.

20. The ventilator system of claim 19, wherein the controller is configured to modulate a control signal for the air flow control valve based on measurement signals received from the oxygen flow sensor and the mixed gas pressure sensor.

21. The ventilator system of claim 19, wherein the controller is configured to modulate a control signal for the air flow control valve based on measurement signals received from the oxygen flow sensor, the air flow sensor and the mixed gas flow sensor.

22. The ventilator system of claim 19, wherein the controller is configured to modulate a control signal for the air flow control valve based on measurement signals received from the oxygen flow sensor, the air flow sensor and an oxygen sensor connected to the mixing chamber.

* * * * *